(12) United States Patent
Fu

(10) Patent No.: US 6,727,274 B2
(45) Date of Patent: Apr. 27, 2004

(54) ARYLSULPHONYL SUBSTITUTED-TETRAHYDRO- AND HEXAHYDRO-CARBAZOLES

(75) Inventor: Jian-Min Fu, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/268,627

(22) Filed: Oct. 8, 2002

(65) Prior Publication Data

US 2003/0100596 A1 May 29, 2003

Related U.S. Application Data

(60) Provisional application No. 60/327,876, filed on Oct. 9, 2001, and provisional application No. 60/327,875, filed on Oct. 9, 2001.

(51) Int. Cl.⁷ ..................... C07D 209/82; A61K 31/40
(52) U.S. Cl. ................. 514/411; 548/439; 548/449
(58) Field of Search ............... 548/439, 449; 514/411

(56) References Cited

U.S. PATENT DOCUMENTS

| | | |
|---|---|---|
| 4,172,834 A | 10/1979 | Mooradian |
| 4,254,134 A | 3/1981 | Fliedner, Jr. |
| 5,827,871 A | 10/1998 | King et al. |
| 5,990,105 A | 11/1999 | Bos et al. |

OTHER PUBLICATIONS

3-Aminotetrahydrocarbazoles as a New Series of Central Nervous System Agents, by Aram Mooradian et al, Journal of Medicinal Chemistry, vol. 20, No. 4, 1997, pp. 487–492.

5-HT₆ Serotonin Receptor Binding Affinities of N₁-Benzenesulfonyl and Related Tryptamines, by Mase Lee et al, Medicinal Chemistry Research, vol. 10, No. 4, 2000, pp. 230–242, Birkhäuser, Boston, US.

*Primary Examiner*—Joseph K. McKane
*Assistant Examiner*—Golam M M Shameem
(74) *Attorney, Agent, or Firm*—Flynn, Thiel, Boutell & Tanis, P.C.

(57) ABSTRACT

The invention provides compounds of formula I for use in treating conditions in which 5-HT₆ receptors are involved such as in anxiety, depression, schizophrenia, Alzheimer's disease, stress-related disease, panic, a phobia, obsessive compulsive disorder, obesity, post-traumatic stress syndrome, epilepsy, and other CNS disorders.

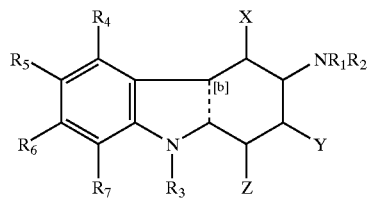

Formula I

29 Claims, No Drawings

ARYLSULPHONYL SUBSTITUTED-TETRAHYDRO- AND HEXAHYDRO-CARBAZOLES

CROSS-REFERENCE TO RELATED APPLICATIONS

This application claims the benefit of U.S. provisional application Ser. No. 60/327,876 and U.S. provisional application Ser. No. 60/327,875, both filed on Oct. 9, 2001, under 35 USC 119(e)(i), which are incorporated herein by reference in their entirety.

FIELD OF THE INVENTION

The present invention relates to substituted 6-arylsulphonyl tetrahydro- and hexahydro-carbazoles which are serotonin receptor, 5-HT$_6$, ligands and are useful for treating anxiety, depression, schizophrenia, Alzheimer's disease, stress-related disease, panic, a phobia, obsessive compulsive disorder, obesity, post-traumatic stress syndrome, epilepsy, and other central nervous system (CNS) disorders in humans and animals.

BACKGROUND

Serotonin has been implicated in a number of diseases, disorders, and conditions that originate in the CNS. Serotonin also plays an important role in peripheral systems, such as the gastrointestinal system, where it has been found to mediate a variety of contractile, secretory, and electrophysiological effects.

Because of the broad distribution of serotonin within the body, a heightened interest exists for drugs that affect serotonergic systems. In particular, agonists, partial agonists, and antagonists of serotonergic systems are of interest for the treatment of a wide range of disorders.

The major classes of serotonin receptors (5-HT$_{1-7}$) contain several separate receptors that have been formally classified. See Glennon, et al., Neuroscience and Behavioral Reviews, 1990, 14, 35; and D. Hoyer, et al. Pharmacol. Rev. 1994, 46, 157–203.

There is currently a need for pharmaceutical agents that are useful to treat diseases and conditions that are associated with 5-HT receptors. In particular, there is a need for agents that can selectively bind to individual receptor sub-types (e.g. receptor-specific agonists or antagonists); such agents would be useful as pharmaceutical agents, or would be useful to facilitate the study of the 5-HT receptor family, or to aid in the identification of other compounds that selectively bind to the specific 5-HT receptors.

For example, the 5-HT$_6$ receptor was identified in 1993 (Monsma et al. Mol. Pharmacol. 1993, 43, 320–327 and Ruat, M. et al. Biochem. Biophys. Res. Com. 1993, 193, 269–276). Several antidepressants and atypical antipsychotics bind to the 5-HT$_6$ receptor with high affinity and this binding may be a factor in their profile of activities (Roth et al. J. Pharm. Exp. Therapeut. 1994, 268, 1403–1410; Sleight et al. Exp. Opin. Ther. Patents 1998, 8, 1217–1224; Bourson et al. Brit. J. Pharm. 1998, 125, 1562–1566; Boess et al. Mol. Pharmacol. 1998, 54, 577–583; Sleight et al. Brit. J. Pharmacol. 1998, 124, 556–562). In addition, the 5-HT$_6$ receptor has been linked to generalized stress and anxiety states (Yoshioka et al. Life Sciences 1998, 17/18, 1473–1477). Together these studies and observations suggest that compounds that antagonize the 5-HT$_6$ receptor will be useful in treating disorders of the central nervous system, such as anxiety, depression, schizophrenia, stress-related disease, panic, a phobia, obsessive compulsive disorder, obesity, post-traumatic stress syndrome, and epilepsy. In general, compounds of formula I, e.g., tetrahydro carbazole compounds including an arylsulphonyl substituent, exhibit selective inhibition of 5-HT$_6$ serotonin receptors relative to the inhibition of other 5-HT serotonin receptors.

General anxiety disorder (GAD) occurs when a person worries about things such as family, health, or work when there is no reason to worry and is unable not to worry. About 3 to 4% of the U.S. population has GAD during the course of a year. GAD most often strikes people in childhood or adolescence, but can begin in adulthood, too. It affects women more often than men. Currently, treatment involves cognitive-behavioral therapy, relaxation techniques, and biofeedback to control muscle tension and medications such as benzodiazepines, imipramine, and buspirone. These drugs are effective but all have side-effect liabilities. Therefore, there is a need of a pharmaceutical agent to address the symptoms with fewer side effects.

Depression is a mood disorder of varying lengths of normally several months to more than two years and of varying degrees of feelings involving sadness, despair, and discouragement. The heterocyclic antidepressants (HCA's) are currently the largest class of antidepressants, but monoamine oxidase inhibitors (MAOI's) are used in particular types of depression. Common side effects from HCA's are sedation and weight gain. In elderly patients with organic brain disease, the side effects from HCA's can also include seizures and behavioral symptoms. The main side effects from using MAOI's occur from dietary and drug interactions. Therefore, agents with fewer side effects would be useful.

Schizophrenia is a disease having multiple aspects. Currently available drugs are generally aimed at controlling the positive aspects of schizophrenia, such as delusions. One drug, Clozapine, is aimed at a broader spectrum of symptoms associated with schizophrenia. This drug has many side effects and is thus not suitable for many patients. Thus, there is a need for a drug to treat the cognitive and attention deficits associated with schizophrenia. Similarly, there is a need for a drug to treat the cognitive and attention deficits associated with schizoaffective disorders, or similar symptoms found in the relatives of schizophrenic patients.

Post-traumatic stress disorder (PTSD) is a form of anxiety triggered by memories of a traumatic event that directly affected the patient or that the patient may have witnessed. The disorder commonly affects survivors of traumatic events including sexual assault, physical assault, war, torture, natural disasters, an automobile accident, an airplane crash, a hostage situation, or a death camp. The affliction also can affect rescue workers at an airplane crash or a mass shooting, someone who witnessed a tragic accident or someone who has unexpectedly lost a loved one. Treatment for PTSD includes cognitive-behavioral therapy, group psychotherapy, and medications such as Clonazepam, Lorazepam and selective serotonin-reuptake inhibitors such as Fluoxetine, Sertraline, Paroxetine, Citalopram and Fluvoxamine. These medications help control anxiety as well as depression. Various forms of exposure therapy (such as systemic desensitization and imaginal flooding) have all been used with PTSD patients. Exposure treatment for PTSD involves repeated reliving of the trauma, under controlled conditions, with the aim of facilitating the processing of the trauma. Therefore, there is a need for better pharmaceutical agents to treat Post traumatic stress disorder.

Stress may increase the release of epinephrine from the adrenal medulla and norepinephrine from adrenergic neurons activated by central nervous system (CNS) stimulation. High levels of circulating epinephrine mediate alpha-adrenergic effects including increases in heart rate and cardiac output. Epinephrine may also be taken up by beta$_2$ receptors on the presynaptic neuronal membrane and may enhance release of norepinephrine from storage granules. Transient epinephrine surges resulting from stress may produce considerably more prolonged vasoconstriction. Stress-induced activation of the sympathetic nervous system may lead to hypertension. Stress also can cause stress gastritis and affect the efficacy of medical treatment in some ulcer patients. There is a need for pharmaceutical agents to treat stress-related diseases.

Panic disorders, phobias, and obsessive compulsive behavior are forms of neurosis. They are all related to excessive anxiety. All humans experience fear and anxiety in response to an external threat, or a difficult situation. However, the neuroses noted above, are abnormal responses to ordinary situations. The causes of such neurotic disorders are not fully known.

Anxiety can arise suddenly, as in panic, or gradually over many minutes, hours, or even days. Anxiety may last for variable periods of time ranging from less than a minute to years. Brief panic attacks are common. However, most persons recover without treatment, and panic disorder is much less common.

Phobias are similar to panic attacks in that they involve anxiety. However, in the various phobias the anxiety is not the free-floating anxiety of panic disorder, but instead focuses on specific situations or stimuli. Persons who have a phobia often realize that their anxiety is excessive, but nonetheless, they tend to avoid the situations or stimuli that disturb them. If they must be exposed to such situations or stimuli they endure them with great distress. Some relatively commonly observed phobias include agoraphobia, that is, the fear of being trapped in closed places, fear of snakes, fear of heights, fear of the dark, fear of strangers, fear of storms, fear of water, heights, and fear of flying.

Persons suffering from an obsessive-compulsive disorder feel compelled to perform repetitive, purposeful, rituals to control their obsessions. For example, a person with an obsessive fear of contamination might compensate with excessive hand washing.

These panic and anxiety disorders may be treated with behavior therapy and antidepressants and benzodiazepines. Obsessive compulsive disorders may be treated with behavior therapy and various drugs such as serotonin reuptake inhibitors (SRIs), selective serotonin reuptake inhibitors (SSRIs—eg, fluoxetine, fluvoxamine, paroxetine, sertraline), and clomipramine (a tricyclic antidepressant) Augmentation with haloperidol, or atypical antipsychotics may be effective. However, these drugs, especially the benzodiazepines and the antipsychotics, have potentially serious side effects. Therefore, there is a need for a pharmaceutical agent to treat these conditions.

Epilepsy is a recurrent, paroxysmal disorder of cerebral function characterized by sudden, brief attacks of altered consciousness, motor activity, sensory phenomena, or inappropriate behavior caused by excessive discharge of cerebral neurons. Treatment aims primarily to control seizures. A causative disorder may need to be treated as well. No single drug controls all types of seizures, and different drugs are required for different patients. Patients rarely require several drugs. Commonly used drugs include phenytoin, carbamazepine, or valproate gabapentin, lamotrigine, and topiramate. Therefore, there is a need for a pharmaceutical agent to treat epilepsy.

Traditionally, obesity has been defined as a body weight of >30% above ideal or desirable weight on standard height-weight tables. Currently, obesity is usually defined in terms of the body mass index (BMI)—weight (in kilograms) divided by the square of the height (in meters). The general cause of obesity is simple—expending less energy than is consumed. However, how people regulate body weight, primarily body fat, is still elusive and not fully understood. Typically, the determinants of obesity are divided into three categories: genetic, environmental, and regulatory. Recent genetic discoveries have helped explain how genes may determine obesity and how they may influence the regulation of body weight. Scientific studies estimate that genetics may account for about 33% of the variation in body weight. The remaining variation may be caused by environmental and regulatory factors. Environmental factors include socio-economic status, large food intake, and sedentary lifestyle. Regulatory factors include pregnancy, endocrine, and psychological influences. Despite the analysis of obesity in terms of these three factors, the final common pathway to caloric balance lies in behavior mediated by the CNS. Recent attempts at pharmacotherapy of obesity has lead to widespread valvular heart disease in patients who received fenfluramine alone or in combination with phentermine (often referred to as fen-phen). Therefore, there is a need for a pharmaceutical agent to treat obesity.

General CNS disease to be treated by the compounds of the present invention include cognitive disorders such as mild cognitive impairment, Alzheimer's disease (AD), and attention deficit disorder with or without hyperactivity. Alzheimer's disease (AD) is a complex disease related with age that slowly progresses to loss of memory and language skills, with the related problems of having difficulties in learning and making decisions and judgments. Approximately 4 million Americans are reported to be suffering from AD. Currently available drugs, tacrine, donepezil and rivostigmine, are used to only retard the progression of the disease. The above-mentioned drugs are to enhance the cholinergic transmission. However, these drugs have serious side effects. There is a need for a drug to treat AD more effectively and have fewer side effects. Meneses, A., Drug News Perspect., 2001, 14, 396–400.

In U.S. Pat. No. 4,172,834, 1,2,3,4-tetrahydrocarbazoles are described as antihistaminic agents. U.S. Pat. No. 5,827,871 discloses 1,2,3,4-tetrahydrocarbazoles that are described as being useful as 5-HT$_1$ like agonist.

SUMMARY OF THE INVENTION

In general, the invention features compounds of Formula I

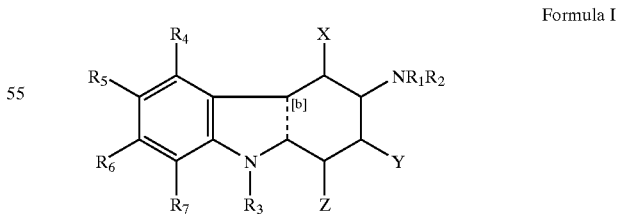

Formula I wherein
- - - [b] is a single or double bond;
Each X, Y, and Z is independently selected from H, —OH, —O-alkyl, and —O-substituted alkyl;
R$_1$ is selected from H, alkyl, substituted alkyl, cycloalkyl, substituted cycloalkyl, and aryl;

$R_2$ is selected from H, alkyl, substituted alkyl, cycloalkyl, substituted cycloalkyl, and aryl;

$R_3$ is selected from H, alkyl, substituted alkyl, cycloalkyl, substituted cycloalkyl, and -A-E-$R_8$;

A is selected from alkyl and substituted alkyl;

E is selected from —N($R_{10}$)C(O)—, —C(O)N($R_{10}$)—, —N($R_{10}$)C(S)—, —C(S)N($R_{10}$)—, —S(O)N($R_{10}$)—, —N($R_{10}$)S(O)—, —S(O)$_2$N($R_{10}$)—, and —N($R_{10}$)S(O)$_2$—;

Each $R_4$, $R_5$, $R_6$, and $R_7$ is independently selected from H, halogen, aryl, —CN, —NO$_2$, alkyl, substituted alkyl, cycloalkyl, substituted cycloalkyl, —OR$_9$, —NH$_2$, —C(O)NH$_2$, —C(S)NH$_2$, and —S(O)$_n$aryl, provided that one of $R_4$, $R_5$, $R_6$, and $R_7$ is —S(O)$_n$aryl, and that at least one of $R_4$, $R_5$, $R_6$, and $R_7$ is H;

n is 0, 1, or 2;

Each $R_8$, $R_9$, and $R_{10}$ is independently selected from H, alkyl, substituted alkyl, cycloalkyl, substituted cycloalkyl, and aryl;

Each $R_{11}$ is independently selected from H, alkyl, substituted alkyl, cycloalkyl, substituted cycloalkyl, heterocycloalkyl, phenyl, naphthyl, and heteroaromatic, provided that any of the alkyl, cycloalkyl, phenyl, naphthyl, or heteroaromatic is optionally substituted with up to 3 substituents independently selected from halogen, alkyl, —CF$_3$, —OR$_{12}$, —SR$_{12}$, —CN, —NO$_2$, —N$_3$, —N(R$_{12}$)$_2$, —C(O)N(R$_{12}$)$_2$, and —C(S)N(R$_{12}$)$_2$;

Each $R_{12}$ is independently selected from H, alkyl, and cycloalkyl, provided that any of the alkyl or cycloalkyl is optionally substituted with up to 2 substituents independently selected from halogen, —CF$_3$, —NO$_2$, —NH$_2$, —N$_3$, —CN, —OH, —O-lower alkyl, and —O-lower substituted alkyl; and pharmaceutically acceptable salts thereof.

Embodiments of the invention may include one or more or combination of the following.

Advantageously, the compounds of Formula I interact with serotonin receptors. Unexpectedly, the compounds of this invention selectively interact with the 5-HT$_6$ serotonin receptor relative to other 5-HT serotonin receptors. Due to the selective interaction with 5-HT$_6$, the compounds of Formula I are useful to treat anxiety, depression, schizophrenia, Alzheimer's disease, stress-related disease, including irritable bowel syndrome, panic, a phobia, obsessive compulsive disorder, obesity, post-traumatic stress syndrome, epilepsy, and other CNS disorders.

Surprisingly, the 3R isomer of the tetrahydro carbazoles of formula I exhibit higher selectivity towards the 5-HT$_6$ serotonin receptor relative to the 3S isomer. One embodiment of the present invention is the group of compounds of Formula I having the 3R stereochemistry. Another embodiment of the present invention is the use of the compounds of Formula I in the treatment of anxiety, depression, schizophrenia, Alzheimer's disease, stress-related disease, panic, a phobia, obsessive compulsive disorder, obesity, post-traumatic stress syndrome, epilepsy, and other CNS disorders.

Another aspect of the present invention is the group of compounds of Formula Ia where the bond represented by - - - and referenced by [b] is a single bond:

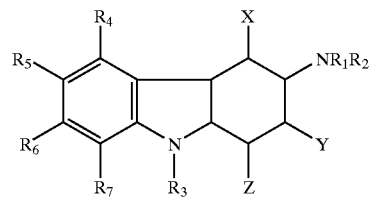

Formula Ia wherein

Each X, Y, and Z is independently selected from H, —OH, —O-alkyl, and —O-substituted alkyl;

$R_1$ is selected from H, alkyl, substituted alkyl, cycloalkyl, substituted cycloalkyl, and aryl;

$R_2$ is selected from H, alkyl, substituted alkyl, cycloalkyl, substituted cycloalkyl, and aryl;

$R_3$ is selected from H, alkyl, substituted alkyl, cycloalkyl, substituted cycloalkyl, and -A-E-$R_8$;

A is selected from alkyl and substituted alkyl;

E is selected from —N($R_{10}$)C(O)—, —C(O)N($R_{10}$)—, —N($R_{10}$)C(S)—, —C(S)N($R_{10}$)—, —S(O)N($R_{10}$)—, —N($R_{10}$)S(O)—, —S(O)$_2$N($R_{10}$)—, and —N($R_{10}$)S(O)$_2$—;

Each $R_4$, $R_5$, $R_6$, and $R_7$ is independently selected from H, halogen, aryl, —CN, —NO$_2$, alkyl, substituted alkyl, cycloalkyl, substituted cycloalkyl, —OR$_9$, —NH$_2$, —C(O)NH$_2$, —C(S)NH$_2$, and —S(O)$_n$aryl, provided that one of $R_4$, $R_5$, $R_6$, and $R_7$ is —S(O)$_n$aryl, and that at least one of $R_4$, $R_5$, $R_6$, and $R_7$ is H;

n is 0, 1, or 2;

Each $R_8$, $R_9$, and $R_{10}$ is independently selected from H, alkyl, substituted alkyl, cycloalkyl, substituted cycloalkyl, and aryl;

Each $R_{11}$ is independently selected from H, alkyl, substituted alkyl, cycloalkyl, substituted cycloalkyl, heterocycloalkyl, phenyl, naphthyl, and heteroaromatic, provided that any of the alkyl, cycloalkyl, phenyl, naphthyl, or heteroaromatic is optionally substituted with up to 3 substituents independently selected from halogen, alkyl, —CF$_3$, —OR$_{12}$, —SR$_{12}$, —CN, —NO$_2$, —N$_3$, —N(R$_{12}$)$_2$, —C(O)N(R$_{12}$)$_2$, and —C(S)N(R$_{12}$)$_2$;

Each $R_{12}$ is independently selected from H, alkyl, and cycloalkyl, provided that any of the alkyl or cycloalkyl is optionally substituted with up to 2 substituents independently selected from halogen, —CF$_3$, —NO$_2$, —NH$_2$, —N$_3$, —CN, —OH, —O-lower alkyl, and —O-lower substituted alkyl; and pharmaceutically acceptable salts thereof.

Another aspect of the present invention is the group of compounds of Formula Ib where the bond represented by - - - and referenced by [b] is a double bond:

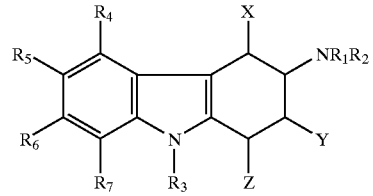

Formula Ib wherein

Each X, Y, and Z is independently selected from H, —OH, —O-alkyl, and —O-substituted alkyl;

$R_1$ is selected from H, alkyl, substituted alkyl, cycloalkyl, substituted cycloalkyl, and aryl;

$R_2$ is selected from H, alkyl, substituted alkyl, cycloalkyl, substituted cycloalkyl, and aryl;

$R_3$ is selected from H, alkyl, substituted alkyl, cycloalkyl, substituted cycloalkyl, and -A-E-$R_8$;

A is selected from alkyl and substituted alkyl;

E is selected from —N($R_{10}$)C(O)—, —C(O)N($R_{10}$)—, —N($R_{10}$)C(S)—, —C(S)N($R_{10}$)—, —S(O)N($R_{10}$)—, —N($R_{10}$)S(O)—, —S(O)$_2$N($R_{10}$)—, and —N($R_{10}$)S(O)$_2$—;

Each $R_4$, $R_5$, $R_6$, and $R_7$ is independently selected from H, halogen, aryl, —CN, —NO$_2$, alkyl, substituted alkyl, cycloalkyl, substituted cycloalkyl, —OR$_9$, —NH$_2$, —C(O)NH$_2$, —C(S)NH$_2$, and —S(O)$_n$aryl, provided that one of $R_4$, $R_5$, $R_6$, and $R_7$ is —S(O)$_n$aryl, and that at least one of $R_4$, $R_5$, $R_6$, and $R_7$ is H;

n is 0, 1, or 2;

Each $R_8$, $R_9$, and $R_{10}$ is independently selected from H, alkyl, substituted alkyl, cycloalkyl, substituted cycloalkyl, and aryl;

Each $R_{11}$ is independently selected from H, alkyl, substituted alkyl, cycloalkyl, substituted cycloalkyl, heterocycloalkyl, phenyl, naphthyl, and heteroaromatic, provided that any of the alkyl, cycloalkyl, phenyl, naphthyl, or heteroaromatic is optionally substituted with up to 3 substituents independently selected from halogen, alkyl, —CF$_3$, —OR$_{12}$, —SR$_{12}$, —CN, —NO$_2$, —N$_3$, —N(R$_{12}$)$_2$, —C(O)N(R$_{12}$)$_2$, and —C(S)N(R$_{12}$)$_2$;

Each $R_{12}$ is independently selected from H, alkyl, and cycloalkyl, provided that any of the alkyl or cycloalkyl is optionally substituted with up to 2 substituents independently selected from halogen, —CF$_3$, —NO$_2$, —NH$_2$, —N$_3$, —CN, —OH, —O-lower alkyl, and —O-lower substituted alkyl; and pharmaceutically acceptable salts thereof.

Another aspect of the present invention is the group of compounds of Formulas I, Ia and Ib where X, Y, and Z are independently any one of the following: H, —OH, —O-alkyl, and —O-substituted alkyl. Another aspect of the present invention is the group of compounds of Formulas I, Ia and Ib where X, Y, and Z are all H. Another aspect of the present invention is the group of compounds of Formulas I, Ia and Ib where any two of X, Y, or Z are H and the other is independently selected from H, —OH, —O-alkyl, and —O-substituted alkyl.

Another aspect of the present invention is the group of compounds of Formulas I, Ia and Ib where one of $R_1$ and $R_2$ is H and the other is selected from any of the following: H, alkyl, substituted alkyl, cycloalkyl, substituted cycloalkyl, and aryl. Another aspect of the present invention is the group of compounds of Formulas I, Ia and Ib where both $R_1$ and $R_2$ are H. Another aspect of the present invention is the group of compounds of Formulas I, Ia and Ib where one of $R_1$ and $R_2$ is H and the other is alkyl. Another aspect of the present invention is the group of compounds of Formulas I, Ia and Ib where one of $R_1$ and $R_2$ is H and the other is lower alkyl, substituted lower alkyl, or cycloalkyl. Another aspect of the present invention is the group of compounds of Formulas I, Ia and Ib where one of $R_1$ and $R_2$ is H and the other is methyl. Another aspect of the present invention is the group of compounds of Formulas I, Ia and Ib where one of $R_1$ and $R_2$ is H and the other is aryl.

Another aspect of the present invention is the group of compounds of Formulas I, Ia and Ib where $R_3$ is any one of the following: H, alkyl, substituted alkyl, cycloalkyl, substituted cycloalkyl, and -A-E-$R_8$. Another aspect of the present invention is the group of compounds of Formulas I, Ia and Ib where A is either alkyl or substituted alkyl. Another aspect of the present invention is the group of compounds of Formulas I, Ia and Ib where E is any one of the following: —N($R_{10}$)C(O)—, —C(O)N($R_{10}$)—, —N($R_{10}$)C(S)—, —C(S)N($R_{10}$)—, —S(O)N($R_{10}$)—, —N($R_{10}$)S(O)—, —S(O)$_2$N($R_{10}$)—, and —N($R_{10}$)S(O)$_2$—.

Another aspect of the present invention is the group of compounds of Formulas I, Ia and Ib where $R_3$ is H. Another aspect of the present invention is the group of compounds where $R_3$ is alkyl, including lower alkyl. Another aspect of the present invention is the group of compounds where $R_3$ is methyl.

Another aspect of the present invention is the group of compounds of Formulas I, Ia and Ib where at least one of $R_4$, $R_5$, $R_6$, and $R_7$ is —S(O)$_n$aryl, where at least one of $R_4$, $R_5$, $R_6$, and $R_7$ is H, and the others are independently any one of the following: H, halogen, aryl, —CN, —NO$_2$, alkyl, substituted alkyl, —OR$_9$, —NH$_2$, —C(O)NH$_2$, —C(S)NH$_2$, and —S(O)$_n$aryl. Another aspect of the present invention is the group of compounds of Formulas I, Ia and Ib where n has any of the following values: 0, 1, or 2.

Another aspect of the present invention is the group of compounds of Formulas I, Ia and Ib where each $R_8$, $R_9$, and $R_{10}$ is independently any one of the following: H, alkyl, substituted alkyl, cycloalkyl, substituted cycloalkyl, and aryl. Another aspect of the present invention is the group of compounds of Formulas I, Ia and Ib where each $R_8$, $R_9$, and $R_{10}$ are H.

Another aspect of the present invention is the group of compounds of Formulas I, Ia and Ib where each $R_{11}$ is independently any one of the following: H, alkyl, substituted alkyl, cycloalkyl, substituted cycloalkyl, heterocycloalkyl, phenyl, naphthyl, and heteroaromatic, provided that any of the alkyl, cycloalkyl, phenyl, naphthyl, or heteroaromatic is optionally substituted with up to 3 substituents independently selected from halogen, alkyl, —CF$_3$, —OR$_{12}$, —SR$_{12}$, —CN, —NO$_2$, —N$_3$, —N(R$_{12}$)$_2$, —C(O)N(R$_{12}$)$_2$, and —C(S)N(R$_{12}$)$_2$;

Another aspect of the present invention is the group of compounds of Formulas I, Ia and Ib where each $R_{12}$ is any one of the following: H, alkyl, and cycloalkyl, provided that any of the alkyl or cycloalkyl is optionally substituted with up to 2 substituents independently selected from halogen, —CF$_3$, —NO$_2$, —NH$_2$, —N$_3$, —CN, —OH, —O-lower alkyl, and —O-lower substituted alkyl;

One of ordinary skill in the art will recognize that where alkyl or substituted alkyl is allowed, lower alkyl or lower substituted alkyl, respectively, is also allowed.

Embodiments of the invention wherein the compound has the Formula Ib as the free base or as a pharmaceutically acceptable salt thereof:

6-(phenylsulfonyl)-2,3,4,9-tertrahydro-1H-carbazol-3-amine;

(3S)-6-(phenylsulfonyl)-2,3,4,9-tertrahydro-1H-carbazol-3-amine;

(3R)-6-(phenylsulfonyl)-2,3,4,9-tertrahydro-1H-carbazol-3-amine;

(3S)-9-methyl-6-(phenylsulfonyl)-2,3,4,9-tertrahydro-1H-carbazol-3-amine;

(3R)-9-methyl-6-(phenylsulfonyl)-2,3,4,9-tertrahydro-1H-carbazol-3-amine;

(3R)-N,9-dimethyl-6-(phenylsulfonyl)-2,3,4,9-tetrahydro-1H-carbazol-3-amine; or (3R)-9-methyl-6-(phenylsulfonyl)-2,3,4,4a-9,9a-hexahydro-1H-carbazol-3-amine.

Embodiments of the invention wherein the compound has the Formula Ia as the free base or as a pharmaceutically acceptable salt thereof;

(3R)-9-methyl-6-(phenylsulfonyl)-2,3,4,4a,9,9a-hexahydro-1H-carbazol-3-amine;

(3S)-9-methyl-6-(phenylsulfonyl)-2,3,4,4a,9,9a-hexahydro-1H-carbazol-3-amine;

(3R)-6-(phenylsulfonyl)-2,3,4,4a,9,9a-hexahydro-1H-carbazol-3-amine;

(3S)-6-(phenylsulfonyl)-2,3,4,4a,9,9a-hexahydro-1H-carbazol-3-amine;

6-(phenylsulfonyl)-2,3,4,4a,9,9a-hexahydro-1H-carbazol;

(3S)-N,9-dimethyl-6-(phenylsulfonyl)-2,3,4,4a,9,9a-hexahydro-1H-carbazol-3-amine;

(3R)-N,9-dimethyl-6-(phenylsulfonyl)-2,3,4,4a,9,9a-hexahydro-1H-carbazol-3-amine;

and pharmaceutically acceptable salts thereof.

Further aspects and embodiments of the invention may become apparent to those skilled in the art from a review of the following detailed description, taken in conjunction with the examples and the appended claims. While the invention is susceptible of embodiments in various forms, described hereafter are specific embodiments of the invention with the understanding that the present disclosure is intended as illustrative, and is not intended to limit the invention to the specific embodiments described herein.

DETAILED DESCRIPTION OF THE INVENTION

In general, the invention features compounds of Formula I:

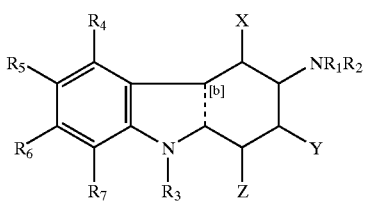

Formula I wherein

- - - [b] is a single or double bond;

Each X, Y, and Z is independently selected from H, —OH, —O-alkyl, and —O-substituted alkyl;

$R_1$ is selected from H, alkyl, substituted alkyl, cycloalkyl, substituted cycloalkyl, and aryl;

$R_2$ is selected from H, alkyl, substituted alkyl, cycloalkyl, substituted cycloalkyl, and aryl;

$R_3$ is selected from H, alkyl, substituted alkyl, cycloalkyl, substituted cycloalkyl, and -A-E-$R_8$;

A is selected from alkyl and substituted alkyl;

E is selected from —N($R_{10}$)C(O)—, —C(O)N($R_{10}$)—, —N($R_{10}$)C(S)—, —C(S)N($R_{10}$)—, —S(O)N($R_{10}$)—, —N($R_{10}$)S(O)—, —S(O)$_2$N($R_{10}$)—, and —N($R_{10}$)S(O)$_2$—;

Each $R_4$, $R_5$, $R_6$, and $R_7$ is independently selected from H, halogen, aryl, —CN, —NO$_2$, alkyl, substituted alkyl, cycloalkyl, substituted cycloalkyl, —OR$_9$, —NH$_2$, —C(O)NH$_2$, —C(S)NH$_2$, and —S(O)$_n$aryl, provided that one of $R_4$, $R_5$, $R_6$, and $R_7$ is —S(O)$_n$aryl, and that at least one of $R_4$, $R_5$, $R_6$, and $R_7$ is H;

n is 0, 1, or 2;

Each $R_8$, $R_9$, and $R_{10}$ is independently selected from H, alkyl, substituted alkyl, cycloalkyl, substituted cycloalkyl, and aryl;

Aryl is phenyl, naphthyl, hetereoaromatic, substituted phenyl, substituted naphthyl, or substituted heteroaromatic;

Heteroaromatic is a 5-, 6-, 9-, or 10-member heteroaromatic mono- or bicyclic ring system containing 1–3 hetero atoms selected from N, O, and S;

Substituted phenyl is phenyl having 1–3 substituents independently selected from halogen, alkyl, substituted alkyl, cycloalkyl, substituted cycloalkyl, —OR$_{11}$, —SR$_{11}$, —CN, —NO$_2$, —N$_3$, —N(R$_{11}$)$_2$, —C(O)N(R$_{11}$)$_2$, —C(S)N(R$_{11}$)$_2$, tetrazole, triazole, amidine, guanidine, thioguanidine, cyanoguanidine, phenyl, naphthyl, and heteroaromatic, provided that any of the phenyl, naphthyl, or heteroaromatic is optionally substituted with up to 3 substituents independently selected from halogen, alkyl, substituted alkyl, cycloalkyl, substituted cycloalkyl, —OR$_{12}$, —SR$_{12}$, —CN, —NO$_2$, —N$_3$, —N(R$_{11}$)$_2$, —C(O)N(R$_{11}$)$_2$, and —C(S)N(R$_{11}$)$_2$;

Substituted naphthyl is naphthyl having 1–6 substituents independently selected from halogen, alkyl, substituted alkyl, cycloalkyl, substituted cycloalkyl, —OR$_{11}$, —SR$_{11}$, —CN, —NO$_2$, —N$_3$, —N(R$_{11}$)$_2$, —C(O)N(R$_{11}$)$_2$, —C(S)N(R$_{11}$)$_2$, tetrazole, triazole, amidine, guanidine, thioguanidine, cyanoguanidine, phenyl, naphthyl, and heteroaromatic, provided that any of the phenyl, naphthyl, or heteroaromatic is optionally substituted with up to 3 substituents independently selected from halogen, alkyl, substituted alkyl, cycloalkyl, substituted cycloalkyl, —OR$_{12}$, —SR$_{12}$, —CN, —NO$_2$, —N$_3$, —N(R$_{11}$)$_2$, —C(O)N(R$_{11}$)$_2$, and —C(S)N(R$_{11}$)$_2$;

Substituted heteroaromatic is the heteroaromatic ring having 1–3 substituents independently selected from halogen, alkyl, substituted alkyl, cycloalkyl, substituted cycloalkyl, —OR$_{11}$, —SR$_{11}$, —CN, —NO$_2$, —N$_3$, —N(R$_{11}$)$_2$, —C(O)N(R$_{11}$)$_2$, —C(S)N(R$_{11}$)$_2$, tetrazole, triazole, amidine, guanidine, thioguanidine, cyanoguanidine, phenyl, naphthyl, and heteroaromatic, provided that any of the phenyl, naphthyl, or heteroaromatic is optionally substituted with 1–3 substituents independently selected from halogen, alkyl, substituted alkyl, cycloalkyl, substituted cycloalkyl, —OR$_{12}$, —SR$_{12}$, —CN, —NO$_2$, —N$_3$, —N(R$_{11}$)$_2$, —C(O)N(R$_{11}$)$_2$, and —C(S)N(R$_{11}$)$_2$;

Alkyl is both straight- and branched-chain moieties having from 1–9 carbon atoms;

Substituted alkyl is the alkyl moiety having at least one substituent having 0–(2n+1) substituents independently selected from —F, —Cl, —Br, and —I, where n is the maximum number of carbon atoms in the moiety and further having 0–1 substituent selected from —CF$_3$, —OR$_{11}$, —SR$_{11}$, —N(R$_{11}$)$_2$, —C(O)R$_{11}$, —C(O)N(R$_{11}$)$_2$, —CN, —NR$_{11}$C(O)R$_{11}$, —S(O)$_2$N(R$_{11}$)$_2$, —NR$_{11}$S(O)$_2$R$_{11}$, —NO$_2$, phenyl, naphthyl, or heteroaromatic, provided that any of the phenyl, naphthyl, or heteroaromatic is optionally substituted with up to 3 substituents independently selected from halogen, alkyl, —$CF_3$, —$OR_{12}$, —$SR_{12}$, CN, $NO_2$, —$N_3$, —$N(R_{11})_2$, —$C(O)N(R_{11})_2$, and —$C(S)N(R_{11})_2$;

Cycloalkyl is a cyclic alkyl moiety having from 3–8 carbon atoms;

Substituted cycloalkyl is the cycloalkyl moiety having at least one substituent having up to 4 substituents independently selected from —F, —Cl, —Br, and —I, and further having up to 1 substituent selected from —$CF_3$, —CN, —$NO_2$, —$OR_{11}$, —$SR_{11}$, —$N(R_{11})_2$, —$C(O)R_{11}$, —$C(O)N(R_{11})_2$, —$NR_{11}C(O)R_{11}$, —$S(O)_2N(R_{11})_2$, —$NR_{11}S(O)_2R_{11}$, phenyl, naphthyl, and heteroaromatic, provided that any of the phenyl, naphthyl, or heteroaromatic is optionally substituted with 1–3 substituents independently selected from halogen, alkyl, —$CF_3$, —$OR_{12}$, —$SR_{12}$, CN, $NO_2$, —$N_3$, —$N(R_{11})_2$, —$C(O)N(R_{11})_2$, and —$C(S)N(R_{11})_2$;

Heterocycloalkyl is a cyclic ring moiety having from 4–7 atoms with 1–2 atoms within the ring selected from N, O, and S;

Each $R_{11}$ is independently selected from H, alkyl, substituted alkyl, cycloalkyl, substituted cycloalkyl, heterocycloalkyl, phenyl, naphthyl, and heteroaromatic, provided that any of the alkyl, cycloalkyl, phenyl, naphthyl, or heteroaromatic is optionally substituted with up to 3 substituents independently selected from halogen, alkyl, —$CF_3$, —$OR_{12}$, —$SR_{12}$, —CN, —$NO_2$, —$N_3$, —$N(R_{12})_2$, —$C(O)N(R_{12})_2$, and —$C(S)N(R_{12})_2$;

Each $R_{12}$ is independently selected from H, alkyl, and cycloalkyl, provided that any of the alkyl or cycloalkyl is optionally substituted with up to 2 substituents independently selected from halogen, —$CF_3$, —$NO_2$, —$NH_2$, —$N_3$, —CN, —OH, —O-lower alkyl, and —O-lower substituted alkyl;

Lower alkyl is both straight- and branched-chain moieties having from 1–4 carbon atoms;

Lower substituted alkyl is the lower alkyl moiety having at least one substituent optionally having up to (2n+1) substituents independently selected from —F, —Cl, —Br, and —I, where n is the maximum number of carbon atoms in the moiety and optionally further having up to 1 substituent independently selected from —$CF_3$, —$NO_2$, —$NH_2$, —CN, —OH, —O-lower alkyl, wherein the lower alkyl of —O-lower alkyl is optionally substituted with 1 substituent selected from —$CF_3$, —$NO_2$, —$NH_2$, —CN, —OH;

and pharmaceutically acceptable salts thereof.

The compounds of Formulas I, Ia and Ib are used to treat anxiety, depression, or other CNS diseases. The arylsulphonyl carbazoles (I, Ia and Ib) are administered orally, sublingually, transdermally or parenterally to provide a dosage of about 0.1 to about 50 mg/kg/day. It is preferred that the dosage range be from about 0.1 to about 10 mg/kg/day. The arylsulphonyl carbazoles (I) can be administered in divided doses either two, three or four times daily. For parenteral administration, a saline solution, dextrose solution, or water may be used as a suitable carrier. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers.

Other adjuvants and modes of administration are well and widely known in the pharmaceutical art. It is preferred that the arylsulphonyl carbazoles (I, Ia and Ib) be administered orally.

The exact dosage and frequency of administration depends on the particular arylsulfonyl carbazole(s) used, the particular disease being treated, the severity of the disease being treated, the age, weight, general physical condition of the particular patient, other medication the individual may be taking as is well known to those skilled in the art and can be more accurately determined by measuring the blood level or concentration of the arylsulphonyl carbazole (I, Ia and Ib) in the patient's blood and/or the patient's response to the particular condition being treated.

The arylsulphonyl carbazole (I, Ia and Ib) compounds of the present invention may be incorporated into pharmaceutical compositions for treating different CNS diseases, such as anxiety or depression. The pharmaceutical compositions may include one or more arylsulphonyl carbazole (I, Ia and Ib) compounds. The compositions also may contain well known carriers and excipients in addition to a therapeutically effective amount of compounds of Formulas I, Ia and Ib. The term "carrier" material or "excipient" herein means any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropyl-methyl cellulose, or other methods known to those skilled in the art. For oral administration, the pharmaceutical composition may be in the form of, for example, a tablet, capsule, suspension or liquid. If desired, other active ingredients may be included in the composition.

In addition to the oral dosing, noted above, the compositions of the present invention may be administered by any suitable route, in the form of a pharmaceutical composition adapted to such a route, and in a dose effective for the treatment intended. The compositions may, for example, be administered parenterally, e.g., intravascularly, intraperitoneally, subcutaneously, or intramuscularly. For parenteral administration, saline solution, dextrose solution, or water may be used as a suitable carrier. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Definitions

Alkyl is both straight- and branched-chain moieties having from 1–9 carbon atoms. For example, $C_{1-9}$ alkyl includes methyl, ethyl, propyl, isopropyl, butyl, iso-butyl, sec-butyl, pentyl, 3-pentyl, hexyl, and isomeric forms thereof.

Examples of heteroaromatic groups include, but are not limited to, thienyl, benzothienyl, pyridyl, thiazolyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, benzoxazolyl, pyrazolyl, triazolyl, tetrazolyl, isoxazolyl, oxazolyl, pyrrolyl, isoquinolinyl, cinnolinyl, indazolyl, indolizinyl, phthalazinyl, pydridazinyl, triazinyl, isoindolyl, purinyl, oxadiazolyl, benzothiophenyl, benzothiazolyl, quinazolinyl, quinoxalinyl, naphthridinyl, and furopyridinyl.

Examples of heterocycloalkyl groups include, but are not limited to, tetrahydrofurano, tetrahydropyrano, morpholino, pyrrolidino, piperidino, piperazine, and

[structure: N-containing six-membered ring with $S(O)_m$]

where m is 0, 1, or 2.

All temperatures are in degrees Centigrade.

HPLC refers to high pressure liquid chromatography.

DMSO refers to dimethylsulfoxide.

DMF refers to dimethylformamide.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

Generally, the following numbering system is used with the compounds of the present invention:

[carbazole numbering structure, positions 1–9]

IR refers to infrared spectroscopy.

NMR refers to nuclear (proton) magnetic resonance spectroscopy, chemical shifts are reported in ppm (δ) downfield from tetramethylsilane.

HRMS refers to high resolution mass spectrometry. FAB refers to fast atom bombardment.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

Compounds of the present invention may be in the form of pharmaceutically acceptable salts. The term "pharmaceutically acceptable salts" refers to salts prepared from pharmaceutically acceptable non-toxic bases including inorganic bases and organic bases, and salts prepared from inorganic acids, and organic acids. Salts derived from inorganic bases include aluminum, ammonium, calcium, ferric, ferrous, lithium, magnesium, potassium, sodium, zinc, and the like. Salts derived from pharmaceutically acceptable organic non-toxic bases include salts of primary, secondary, and tertiary amines, substituted amines including naturally occurring substituted amines, cyclic amines, such as arginine, betaine, caffeine, choline, N, N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and the like. Salts derived from inorganic acids include salts of hydrochloric acid, hydrobromic acid, hydroiodic acid, sulfuric acid, phosphoric acid, phosphorous acid and the like. Salts derived from pharmaceutically acceptable organic non-toxic acids include salts of $C_{1-6}$ alkyl carboxylic acids, di-carboxylic acids, and tri-carboxylic acids such as acetic acid, propionic acid, fumaric acid, succinic acid, tartaric acid, maleic acid, adipic acid, and citric acid, and aryl and alkyl sulfonic acids such as toluene sulfonic acids and the like.

By the term "effective amount" of a compound as provided herein is meant a nontoxic but sufficient amount of the compound(s) to provide the desired effect. As pointed out below, the exact amount required will vary from subject to subject, depending on the species, age, and general condition of the subject, the severity of the disease that is being treated, the particular compound(s) used, the mode of administration, and the like. Thus, it is not possible to specify an exact "effective amount." However, an appropriate effective amount may be determined by one of ordinary skill in the art using only routine experimentation.

Preparation of Arylsulphonyl Substituted Carbazoles

Compounds of Formulas I, Ia and Ib of the present invention may be prepared using the following reaction schemes:

Arylsulphonylphenylhydrazines can be prepared by the reactions outlined in Scheme 1.

Scheme 1

ArSH + (1) → [Cl-substituted nitrobenzene with R] (2) → Ar-S-[phenyl with R and $NO_2$] (3)

↓

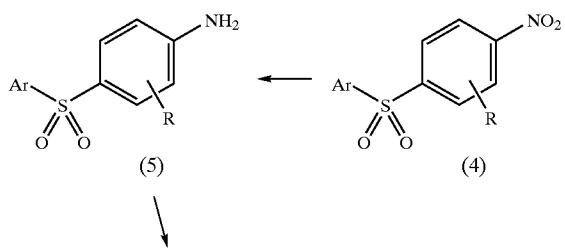

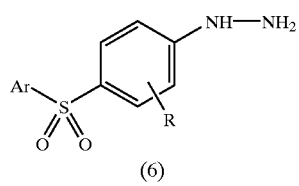

The appropriately substituted thiols (1) are either known to those skilled in the art or can be readily prepared from known starting materials by means well known to those skilled in the art. Thiol (1) can be coupled with the appropriately substituted nitrobenzene, e.g., 4-chloro-1-nitrobenzene (2), by known means to produce the thioether (3). Only one arylsulphonyl group, e.g., $R_5$ in Formula I, and one R group, e.g., one of $R_4$, $R_6$, and $R_7$, are shown. For simplicity, the other R groups are not shown. Typically if $R_4$, $R_6$, and $R_7$ are substituents other than —H, those moieties should be part of the substituted nitrobenzene (2) so that they become incorporated into the unsubstituted arylsulfone (10) when it is formed. In general, adding phenyl substitutents (other than —H) to the unsubstituted arylsulfone (10) once it is formed is difficult. The substitution pattern at the C-5, C-6, C-7, and C-8 positions of the carbazoles of Formulas I, Ia and Ib can be produced by varying the substitution pattern on the substituted nitrobenzene.

Oxidizing the thioether (3) with oxone followed by hydrogenation with rhodium on carbon (5%), all of which is known to those skilled in the art, produce the amine (5). The amine (5) can be diazotized by (sodium) nitrite and (hydrochloric) acid followed by reduction with tin chloride to give the corresponding hydrazine (6).

Scheme 2 illustrates a schematic synthesis for preparing compound (9). Reaction of 4-aminocyclohexanol (7) with N-carbethoxyphthalimide produces the phthalimide compound (8), which when oxidized with an oxidant such as pyridinium chlorochromate (PCC) provides ketone (9).

Scheme 2

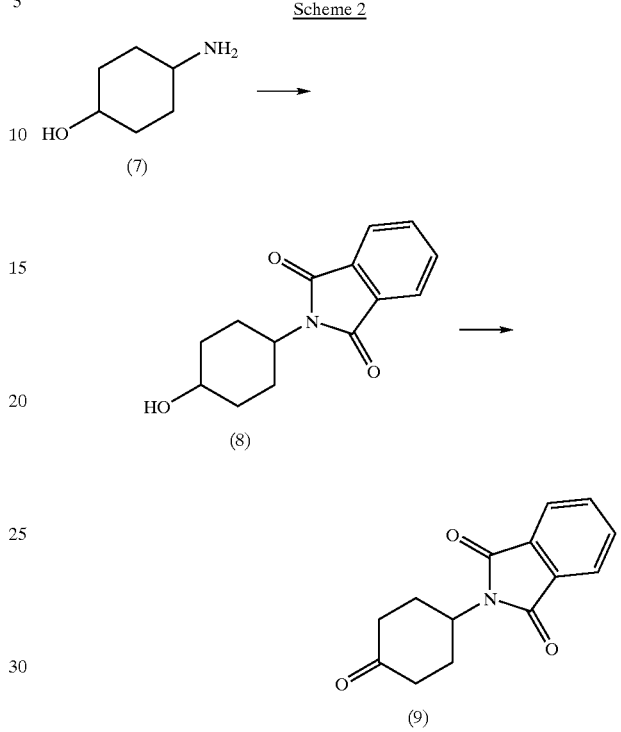

Compounds of formula I can be prepared by the reactions outlined in Scheme 3 (where $R_1=R_2=R_3=R_4=R_6=R_7=H$) Fisher indole synthesis using hydrazine (6) and cyclohexanone (9) generates indole (10). The phthalimide group can be removed by reaction with hydrazine to produce the free amine (11). For convenience of resolution on a chiral column, the amino group can be protected to form the Boc protected compound (12), which, in turn, can be subjected to HPLC. After separation, individually treating the two enantiomers (13) and (14) with acid, such as hydrochloric acid, provides the hydrochloride salt of amines (15) and (16), respectively.

Scheme 3

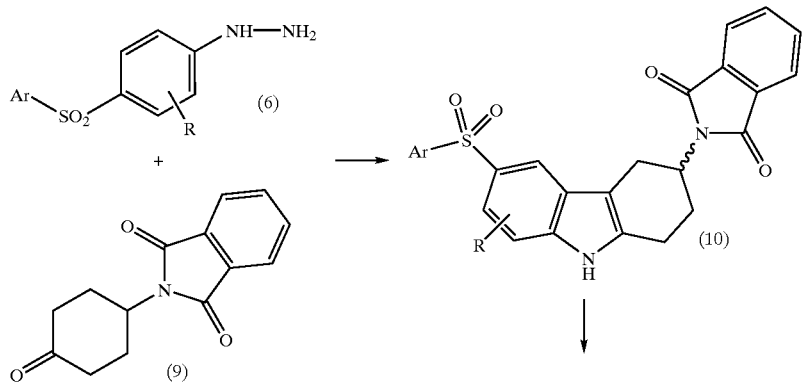

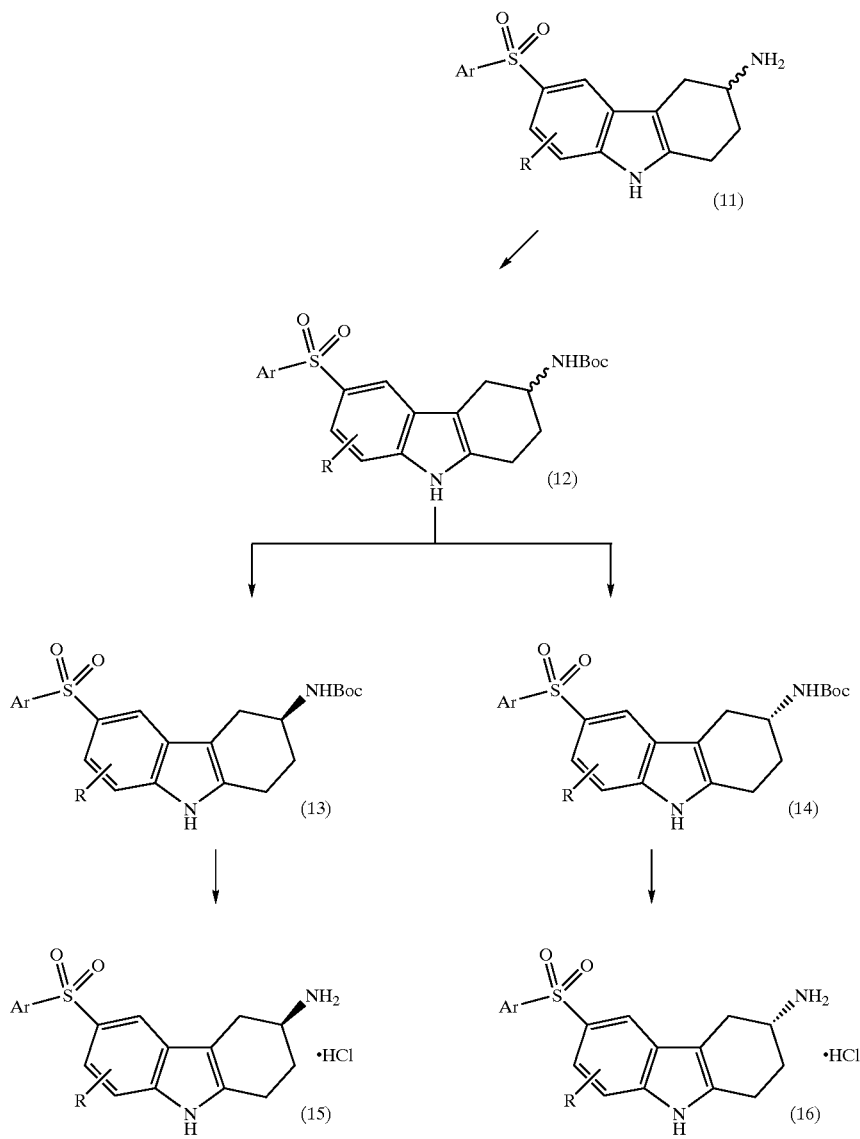

Compounds of Formulas I, Ia and Ib can also be prepared by the reactions outlined in Scheme 4. The $R_3$ group such as an alkyl can be introduced on the indole nitrogen by treating compound (10) with sodium hydride and electrophiles to produce compound (17). After deprotection with hydrazine, resolving the free amine (18) on a chiral column generates the two enantiomers (19) and (20), which can also be protected with a protecting group such as Boc. The $R_1$ group can be introduced by reacting 21 (or 22) with a base such as sodium hydride and quenched with an electrophile. After removing the protecting group (Boc) under acidic conditions, such as with hydrochloric acid, reductive amination with an aldehyde in the presence of a reducing agent such as sodium cyanoborohydride (see for example Lane, C. F., "Sodium Cyanoborohydride—A Highly Selective Reducing Agent for Organic Functional Groups", Synthesis, 1975, 135) provides the tertiary amines 27 and 28, respectively.

Scheme 4

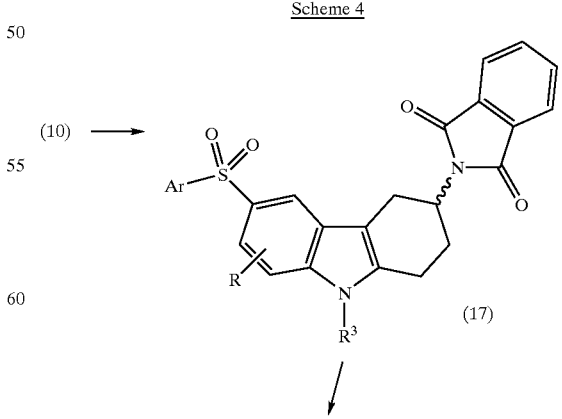

Scheme 5

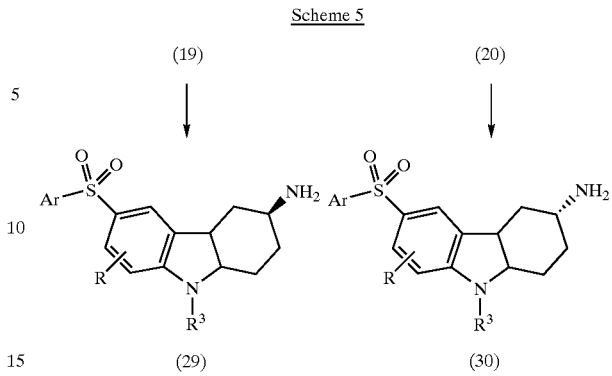

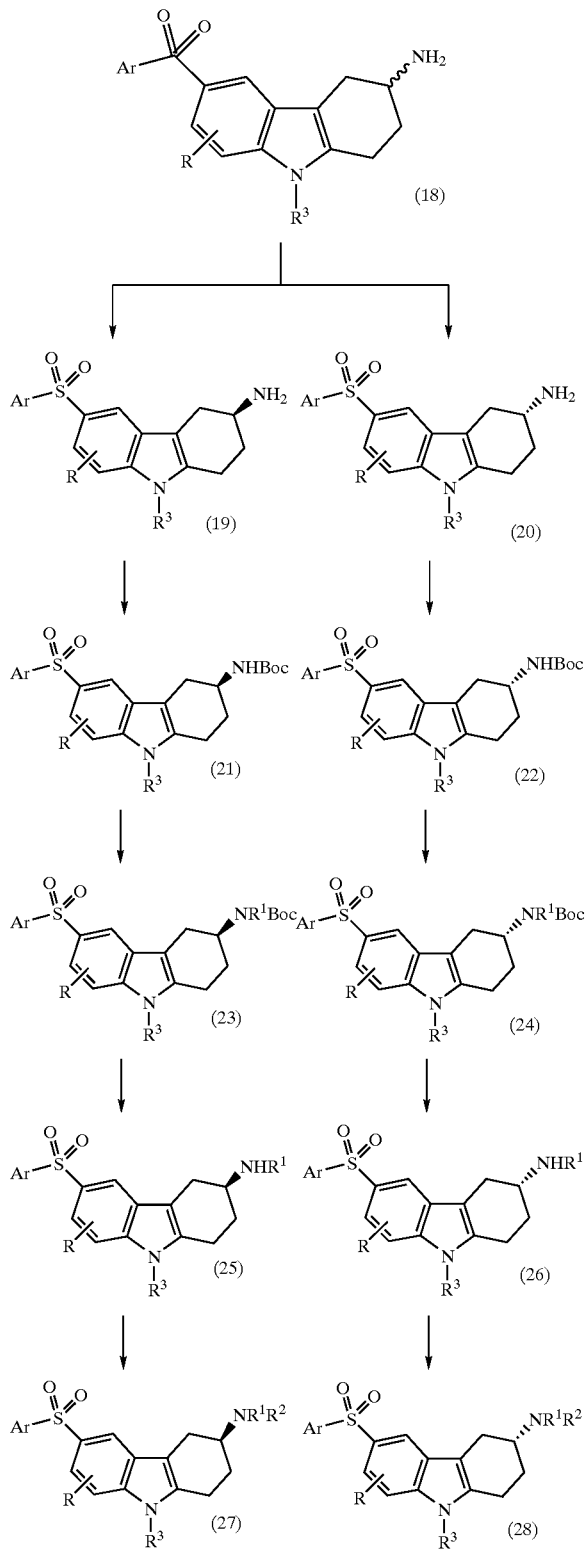

Compounds of Formula Ia where - - - [b] is a single bond which can be prepared by the reactions outlined in Scheme 5. The resolved amino compounds 19 (or 20) can be treated with a reducing reagent such as sodium cyanoborohydride in an acid media such as trifluoroacetic acid or acetic acid to lead to the formation of the indoline compounds 29 (or 30).

The invention also includes isotopically-labeled compounds, which are identical to those recited in Formulas I, Ia and Ib but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3$H, $^{11}$C, $^{14}$C, $^{13}$N, $^{15}$O, $^{18}$F, $^{99m}$Tc, $^{123}$I, and $^{125}$I. Compounds of the present invention and pharmaceutically acceptable salts and prodrugs of said compounds that contain the aforementioned isotopes and/or other isotopes of other atoms are within the scope of the invention. Isotopically-labeled compounds of the present invention are useful in drug and/or substrate tissue distribution and target occupancy assays. For example, isotopically labeled compounds are particularly useful in SPECT (single photon emission computed tomography) and in PET (positron emission tomography).

Single-photon emission computed tomography (SPECT), acquires information on the concentration of isotopically labeled compounds introduced to a mammal's body. SPECT dates from the early 1960's, when the idea of emission traverse section tomography was introduced by D. E. Kuhl and R. Q. Edwards prior to either PET, x-ray CT, or MRI. In general, SPECT requires isotopes that decay by electron capture and/or gamma emission. Example of viable SPECT isotopes include, but are not limited to, 123-iodine ($^{123}$I) and 99m-technetium ($^{99m}$Tc). Subjects are injected with a radioactively labeled agent, typically at tracer doses. The nuclear decay resulting in the emission of a single gamma ray which passes through the tissue and is measured externally with a SPECT camera. The uptake of radioactivity reconstructed by computers as a tomogram shows tissue distribution in cross-sectional images.

Positron emission tomography (PET) is a technique for measuring the concentrations of positron-emitting isotopes within the tissues. Like SPECT, these measurements are, typically, made using PET cameras outside of the living subjects. PET can be broken down into several steps including, but not limited to, synthesizing a compound to include a positron-emitting isotope; administering the isotopically labeled compound to a mammal; and imaging the distribution of the positron activity as a function of time by emission tomography. PET is described, for example, by Alavi et al. in Positron Emission Tomography. published by Alan R. Liss, Inc. in 1985.

Positron-emitting isotopes used in PET include, but are not limited to, Carbon-11, Nitrogen-13, Oxygen-15, and Fluorine-18. In general, positron-emitting isotopes should have short half-lives to help minimize the long term radiation exposure that a patient receives from high dosages required during PET imaging.

In certain instances, PET imaging can be used to measure the binding kinetics of compounds of this invention with 5-HT$_6$ serotonin receptors. For example, administering an isotopically labeled compound of the invention that penetrates into the body and binds to a 5-HT$_6$ serotonin receptor creates a baseline PET signal which can be monitored while administering a second, different, non-isotopically labeled compound. The baseline PET signal will decrease as the non-isotopically labeled compound competes for the binding to the 5-HT$_6$ serotonin receptor.

In general, compounds of formula I that are useful in performing PET or SPECT are those which penetrate the blood-brain barrier, exhibit high selectivity and modest affinity to 5-HT$_6$ serotonin receptors, and are eventually metabolized. Compounds that are non-selective or those that exhibit excessive or small affinity for 5-HT$_6$ serotonin receptors, are generally, not useful in studying brain receptor binding kinetics with respect to 5-HT$_6$ serotonin receptors. Compounds that are not metabolized may harm the patient.

In other embodiments, nuclear magnetic resonance spectroscopy (MRS) imaging can be used to detect the overall concentration of a compound or fragment thereof containing nuclei with a specific spin. In general, the isotopes useful in NMR imaging include, but are not limited to, hydrogen-1, carbon-13, phosphorus-31, and fluorine-19.

Further, substitution with heavier isotopes such as deuterium, i.e., $^2$H, can afford certain therapeutic advantages resulting from greater metabolic stability, for example increased in vivo half-life or reduced dosage requirements and, hence, maybe preferred in some circumstances. Isotopically labeled compounds of Formula I of this invention can generally be prepared by carrying out the synthetic procedures described above by substituting an isotopically labeled reagent for a non-isotopically labeled reagent.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Preparation 1: 2-(4-Oxocyclohexyl)-1H-isoindole-1,3(2H)-dione:

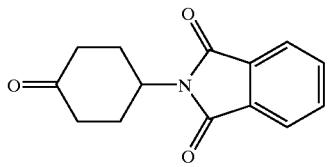

Step 1:

A solution of 4-aminocyclohexanol hydrochloride (2.52 g, 16.6 mmol) in water (20.0 mL) was treated with N-carbethoxyphthalimide (3.82 g, 17.4 mmol) and Na$_2$CO$_3$ (3.77 g, 35.6 mmol). The reaction was stirred at room temperature for 15.6 hours. The reaction was cooled to 0° C. and quenched with 10% HCl, filtered, and washed with water to give a white solid. The solid was dissolved in ethyl acetate washed with water, brine, dried over MgSO4 and concentrated in vacuo to give 3.10 g (76%) of 2-(4-hydroxycyclohexyl)-1H-isoindole-1,3(2H)-dione as a colorless solid: mp 176.9–177.0° C.; $^1$H NMR (400 MHz, Acetone-d$_6$) δ 7.82 4.09, 3.74, 3.62, 2.28, 2.04, 1.76, 1.39; $^{13}$C NMR (100 MHz, acetone-d$_6$) δ 168.7, 135.1, 133.0, 123.6, 69.5, 50.8, 35.7, 28.3; IR (mull) 3389, 3318, 2953, 2930, 2876, 2861, 1767, 1703, 1463, 1393, 1377, 1088, 1075, 1061, 720 cm$^{-1}$; HRMS (FAB) calcd for C$_{14}$H$_{16}$NO$_3$: 246.1130, found 246.1128; Anal. Calcd for C$_{14}$H$_{15}$NO$_3$: C, 68.56; H, 6.16; N, 5.71. Found: C, 68.39; H, 6.21; N, 5.70.

Step 2:

A solution of 2-(4-hydroxycyclohexyl)-1H-isoindole-1,3(2H)-dione (3.10 g, 12.6 mmol) in CH$_2$Cl$_2$ (25.0 mL) was added to a slurry of PCC (4.10 g, 19.0 mmol) in CH$_2$Cl$_2$ (15.0 mL) and stirred at room temperature for 3.5 hours. The reaction was diluted with Et$_2$O (60.0 mL), decanted and the residue swirled with Et$_2$O (2×40.0 mL). The combined ether layers were filtered through florisil and concentrated in vacuo to dryness, and the residue was recrystallized from ethyl acetate/hexane to give 2.01 g (65%) of 2-(4-oxocyclohexyl)-1H-isoindole-1,3(2H)-dione as colorless needles: mp 140.3–142.1° C.; $^1$H NMR (400 MHz, CDCl$_3$) δ 7.84, 7.74, 4.64, 2.72, 2.54, 2.09; $^{13}$C NMR (100 MHz, CDCl$_3$) δ 208.9, 168.1, 134.1, 131.9, 123.3, 48.4, 39.9, 28.6; IR (mull) 3062, 3031, 2958, 2949, 2919, 2885, 1775, 1762, 1721, 1708, 1611, 1465, 1436, 1419, 1393, 1379, 719 cm$^{-1}$; HRMS (FAB) calcd for C$_{14}$H$_{14}$NO$_3$: 244.0974, found 244.0976; Anal. Calcd for C$_{14}$H$_{14}$NO$_3$: C, 69.12; H, 5.39; N, 5.76. Found: C, 68.87; H, 5.47; N, 5.73.

Example 1
6-(Phenylsulfonyl)-2,3,4,9-tertrahydro-1H-carbazol-3-amine Hydrochloride (Racemic):

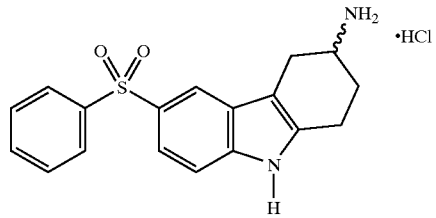

Step 1:

A solution of 2-(4-oxocyclohexyl)-1H-isoindole-1,3[2H]-dione (3.99 g, 16.4 mmol) and 1-[4-(phenylsulfonyl)phenyl]hydrazine (3.69 g, 14.9 mmol) in formic acid (45.0 mL) was heated to reflux for 15.4 hours then cooled to room temperature, diluted with ethyl acetate, filtered and concentrated in vacuo to give 2.678 g (39%) of (rac)-2-[6-(phenylsulfonyl)-2,3,4,9-tertrahydro-1H-carbazol-3-yl]-1H-isoindole-1,3[2H]-dione as colorless solid. The filtrate was concentrated in vacuo and subjected to column chromatography (EtOAc/hexane, 1:1 and 1% triethylamine) to give an additional 0.57 g (8%) of the title compound: mp>275° C.; $^1$H NMR (400 MHz, DMSO-d$_6$) δ 11.50, 8.00, 7.90, 7.55, 7.47, 4.49, 3.31, 2.95, 2.68, 2.12; $^{13}$C NMR (100 MHz, DMSO-d$_6$) δ 167.8, 142.8, 138.3, 136.9, 134.4, 132.7, 131.4, 130.4, 129.3, 126.7, 126.4, 122.9, 119.3, 117.8, 111.5, 108.3, 47.3, 26.0, 24.1, 22.3; IR (drift) 2482, 1989, 1710, 1392, 1374, 1342, 1305, 1154, 1109, 1092, 760, 739, 716, 684, 629 cm$^{-1}$; HRMS (FAB) calcd for C$_{26}$H$_{20}$N$_2$O$_4$S+H 457.1222, found 457.1239; Anal. Calcd for C$_{26}$H$_{20}$N$_2$O$_4$S: C, 68.40; H, 4.42; N, 6.14; S, 7.02. Found: C, 68.38; H, 4.47; N, 6.13.

Step 2:

To a solution of (rac)-2-[6-(phenylsulfonyl)-2,3,4,9-tertrahydro-1H-carbazol-3-yl]-1H-isoindole-1,3[2H]-dione (3.23 g, 7.1 mmol) in methanol (70.0 mL) was added hydrazine hydrate (6.6 mL, 136 mmol). After stirring at room temperature for 2.3 hours the reaction was concentrated in vacuo to dryness. The residue was stirred with $CH_2Cl_2$ for 0.7 hours. The undissolved solid was removed by filtration, and the filtrate was washed with water, brine, and concentrated in vacuo to give 1.59 g (69%) of colorless solid. The colorless solid (0.26 g, 0.80 mmol) was treated with a 4.0 N HCl in dioxane (10.0 mL) and stirred at room temperature for 6.5 hours. After the reaction mixture was concentrated in vacuo, methanol was added, and the solution was concentrated in vacuo and recrystallized from $CH_3OH$/ethyl acetate to give 0.063 g (22%) of 6-(phenylsulfonyl)-2,3,4,9-tetrahydro-1H-carbazol-3-amine hydrochloride (racemic) as a light yellow solid: mp 205–211° C.; $^1H$ NMR (400 MHz, DMSO-$d_6$) δ 11.60, 8.40, 8.03, 7.93, 7.57, 7.47, 3.53, 3.13, 2.86, 2.79, 2.20, 1.97; $^{13}C$ NMR (100 MHz, DMSO-$d_6$) δ 42.8, 138.2, 136.6, 132.8, 130.5, 129.4, 126.7, 126.2, 119.4, 117.7, 111.6, 106.4, 46.5, 26.3, 25.2, 20.3; IR (drift) 3445, 3404, 3228, 3146, 2947, 2932, 2906, 2842, 1298, 1153, 1143, 1130, 1093, 732, 688 $cm^{-1}$; HRMS (FAB) calcd for $C_{18}H_{18}N_2O_2S+H$: 327.1167, found 327.1166; Anal. Calcd for $C_{18}H_{18}N_2O_2S \cdot HCl \cdot 1.2H_2O$: C, 56.23; H, 5.61; N, 7.29. Found: C, 56.32; H, 5.71; N, 7.39.

Example 2

(3S)-6-(Phenylsulfonyl)-2,3,4,9-tertrahydro-1H-carbazol-3-amine Hydrochloride and (3R)-6-(Phenylsulfonyl)-2,3,4,9-tertrahydro-1H-carbazol-3-amine Hydrochloride:

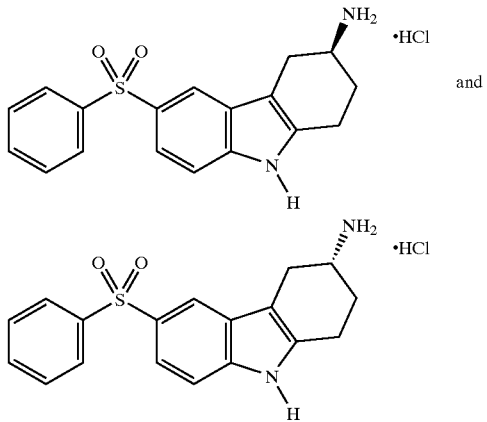

Step 1:

Di-tert-butyl dicarbonate (1.09 g, 4.98 mmol) was added to a solution of (rac)-6-(phenylsulfonyl)-2,3,4,9-tertrahydro-1H-carbazol-3-amine (1.29 mg, 3.96 mmol) in $CH_2Cl_2$ (30.0 mL). The reaction was stirred at room temperature for 2.2 hours then washed with water, saturated $NaHCO_3$, brine, dried over $MgSO_4$ and concentrated in vacuo to a brown oil. The oil was subjected to column chromatography (50% ethyl acetate/hexane) to give 1.39 g (82%) of (rac) tert-butyl 6-(phenylsulfonyl)-2,3,4,9-tertrahydro-1H-carbazol-3-ylcarbamate as a colorless solid. The racemic mixture was separated into the two enantiomers on HPLC by using a chiral column: 0.46×25 cm chiralpak AD, eluted with 20% isopropanol/hexane at 0.5 mL/min, detector set at 280 nM.

Fraction 1 (the first-eluting fraction, 0.62 g, 37%): mp 133.8–137.8° C. $^1H$ NMR (400 MHz, $CDCl_3$) δ 8.39, 8.06, 7.93, 7.62, 7.46, 7.32, 4.72, 4.05, 3.06, 2.80, 2.58, 2.09, 1.92, 1.47; $^{13}C$ NMR (100 MHz, $CDCl_3$) δ 155.5, 143.0, 138.4, 135.8, 132.5, 131.6, 129.1, 127.4, 127.2, 120.5, 118.8, 111.2, 109.3, 79.5, 46.3, 28.5, 28.47, 27.9, 20.9; IR (drift) 3275, 1678, 1510, 1478, 1368, 1337, 1314, 1291, 1263, 1157, 1133, 1091, 727, 687, 640 $cm^{-1}$; Anal. Calcd for $C_{23}H_{26}N_2O_4S$: C, 64.77; H, 6.14; N, 6.57. Found: C, 64.53; H, 6.24; N, 6.57.

Fraction 2 (0.55 g, 33%): mp 135.7–139.4° C.; $^1H$ NMR (400 MHz, $CDCl_3$) δ 8.39, 8.06, 7.92, 7.62, 7.45, 7.32, 4.72, 4.05, 3.06, 2.80, 2.56, 2.09, 1.92, 1.47; $^{13}C$ NMR (100 MHz, $CDCl_3$) δ 155.5, 143.0, 138.4, 135.8, 132.5, 131.6, 129.1, 127.4, 127.2, 120.5, 118.8, 111.1, 109.3, 79.5, 46.3, 28.5, 28.4, 27.9, 20.9; IR (drift) 3275, 1678, 1510, 1478, 1368, 1314, 1291, 1263, 1245, 1156, 1133, 1091, 727, 687, 640 $cm^{-1}$; Anal. Calcd for $C_{23}H_{26}N_2O_4$-S: C, 64.77; H, 6.14; N, 6.57. Found: C, 64.56; H, 6.23; N, 6.55.

The stereochemistry of Fractions 1 and 2 were not identified.

Step 2:

Fraction 1 from Step 1 above (0.59 g, 1.38 mmol) was dissolved in 4.0 N HCl in dioxane (5.0 mL) and stirred at room temperature for 15.6 hours. After the reaction mixture was concentrated in vacuo, methanol was added and the solution was concentrated in vacuo and recrystallized from $CH_3OH$/ethyl acetate to give 0.39 g (78%) of one isomer of Example 2 as a colorless solid: mp 216–218° C.; $^1H$ NMR (400 MHz, DMSO-$d_6$) δ 11.60, 8.37, 8.03, 7.92, 7.57, 7.47, 3.57, 3.13, 2.86, 2.78, 2.20, 1.96; $^{13}C$ NMR (100 MHz, DMSO-$d_6$) δ 142.8, 138.2, 136.6, 132.8, 130.5, 129.4, 126.7, 126.2, 119.4, 117.7, 111.6, 106.4, 46.5, 26.3, 25.2, 20.3; IR (drift) 3334, 3218, 3158, 3054, 3002, 2924, 2903, 2850, 1476, 1299, 1151, 1131, 1092, 731, 613 $cm^{-1}$; HRMS (FAB) calcd for $C_{18}H_{18}N_2O_2S+H$: 327.1167, found 327.1167; Anal. Calcd for $C_{18}H_{18}N_2O_2S \cdot HCl \cdot 0.5EtOAc \cdot 0.75H_2O$: C, 57.14; Hi 5.87; N, 6.66. Found: C, 57.19; H, 6.00; N, 6.73.

Following the general procedure of Step 2, starting with Fraction 2 from Step 1 above, making non-critical variations, the other isomer of Example 2 was obtained as a colorless solid (79%): mp 224–227° C.; $^1H$ NMR (400 MHz, DMSO-d6) δ 11.60, 8.37, 8.04, 7.92, 7.57, 7.47, 3.57, 3.13, 2.86, 2.79, 2.20, 1.96; $^{13}C$ NMR (100 MHz, DMSO-$d_6$) δ 142.8, 138.2, 136.6, 132.8, 130.5, 129.4, 126.7, 126.2, 119.4, 117.7, 111.6, 106.4, 46.5, 26.3, 25.2, 20.3; IR (drift) 3218, 3156, 3053, 3003, 2924, 2907, 2853, 1477, 1299, 1152, 1131, 1093, 731, 688, 613 $cm^{-1}$; HRMS (FAB) calcd for $C_{18}H_{18}N_2O_2S+H$: 327.1167, found 327.1175; Anal. Calcd for $C_{18}H_{18}N_2O_2S \cdot HCl \cdot 0.35 EtOAc \cdot 0.35H_2O \cdot 0.40CH_3OH$: C, 57.61; H, 5.88; N, 6.79. Found: C, 57.59; H, 6.06; N, 6.78.

Example 3(a)

(3R)-9-Methyl-6-(phenylsulfonyl)-2,3,4,9-tertrahydro-1H-carbazol-3-amine:

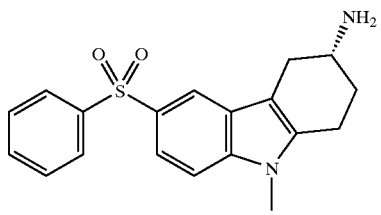

Example 3(b)

(3S)-9-Methyl-6-(phenylsulfonyl)-2,3,4,9-tertrahydro-1H-carbazol-3-amine:

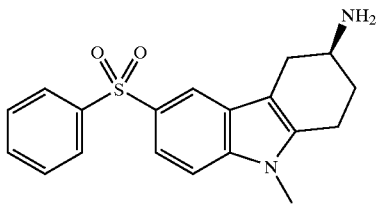

Step 1:

A solution of (rac)-2-[6-(phenylsulfonyl)-2,3,4,9-tertrahydro-1H-carbazol-3-yl]-1H-isoindole-1,3[2H]-dione (2.93 g, 6.4 mmol) in DMF (10.0 mL) was added to a 0° C. suspension of 60% sodium hydride (0.51 g, 12.7 mmol) in DMF (3.0 mL) and stirred for 0.4 hours. Methyl iodide (1.50 g, 10.6 mmol) was added, and the reaction was stirred at room temperature for 3.67 hours. The reaction was quenched with water and extracted with $CH_2Cl_2$. The $CH_2Cl_2$ extracts were washed with water, brine, and the dried over $MgSO_4$ and concentrated in vacuo to give 1.74 g (58%) of (rac)-2-[9-methyl-6-(phenylsulfonyl)-2,3,4,9-tertrahydro-1H-carbazol-3-yl]-1H-isoindole-1,3[2H]-dione as a colorless solid: $^1$H NMR (400 MHz, DMSO-$d_6$) δ 8.06, 7.97–7.88, 7.66–7.55, 4.49, 3.70, 3.38–3.33, 3.05–3.01, 2.88–2.86, 2.75–2.70, 2.21; $^{13}$C NMR (100 MHz, DMSO-$d_6$) δ 168.1, 143.2, 139.1, 138.5, 134.6, 132.9, 131.8, 130.9, 129.5, 127.0, 126.0, 123.1, 119.4, 118.2, 110.3, 108.4, 47.4, 26.2, 24.3, 21.5; IR (drift) 1710 (s), 1391, 1373, 1303, 1151, 1113, 1089, 814, 743, 719, 692, 644, 638, 618, 611 cm$^{-1}$; HRMS (FAB) calcd for $C_{27}H_{22}N_2O_4S$+H: 471.1378, found: 471.1383; Anal. Calcd for $C_{27}H_{22}N_2O_4S$: C, 68.92; H, 4.71; N, 5.95. Found: C, 68.50; H, 4.82; N, 5.88.

Step 2:

To a solution of (rac) 2-[9-methyl-6-(phenylsulfonyl)-2,3,4,9-tertrahydro-1H-carbazol-3-yl]-1H-isoindole-1,3[2H]-dione (1.70 g, 3.6 mmol) in methanol (100 mL) was added hydrazine hydrate (1.6 mL, 33 mmol). After stirring at room temperature for 4.75 hours, the reaction was concentrated in vacuo. The residue was dissolved in $CH_2Cl_2$ and concentrated in vacuo to give 0.77 g (63%) of (rac) 9-methyl-6-(phenylsulfonyl)-2,3,4,9-tertrahydro-1H-carbazol-3-amine as a yellow oil, which was separated into enantiomers on HPLC by using a chiral column: 0.46×25 cm chiralpack AD, eluted with 0.05% diethylamine/ethanol at 0.5 mL/min, dector set at 280 nM.

Example 3(a)

Fraction 1: (First-eluting fraction, 86 mg, 7%); mp 189.3–193.2° C.; $[α]_D$=+29° (C 1.04, DMSO) $^1$H NMR (400 MHz, DMSO-$d_6$) δ 8.04, 7.94–7.92, 7.63–7.54, 3.64, 3.39–3.06, 2.91–2.79, 2.66–2.60, 2.14, 1.88; $^{13}$C NMR (100 MHz, DMSO-$d_6$) δ 142.7, 138.6, 138.1, 132.8, 130.5, 129.4, 126.7, 125.7, 119.2, 117.7, 110.1, 107.1, 46.5, 29.3, 27.9, 26.8, 19.4; IR (drift) 3225, 3217, 3156, 3054, 2998, 2931, 1611, 1482, 1377, 1312, 1304, 1151, 1091, 729, 624 cm$^{-1}$; HRMS (FAB) calcd for $C_{19}H_{20}N_2O_2S$+H: 341.1324, found: 341.1323; Anal. Calcd for $C_{19}H_{20}N_2O_2S·2H_2O$: C, 60.62; H, 6.43; N, 7.44. Found: C, 60.36; H, 5.95; N, 7.51.

Example 3(b)

Fraction 2: (114 mg, 9%); $[α]_D$=−30° (C 1.02, DMSO) $^1$H NMR (400 MHz, DMSO-$d_6$) δ 8.04, 7.94–7.92, 7.63–7.54, 3.64, 3.39–3.06, 2.91–2.79, 2.66–2.60, 2.14, 1.88; $^{13}$C NMR (100 MHz, DMSO-$d_6$) δ 142.7, 138.6, 138.1, 132.8, 130.5, 129.4, 126.7, 125.7, 119.2, 117.8, 110.1, 106.9, 46.5, 29.3, 27.6, 26.5, 19.4; IR (drift) 3055, 3015, 2999, 2931, 2849, 1613, 1481, 1377, 1304, 1150, 1092, 730, 690, 624, 609 cm$^{-1}$; HRMS (FAB) calcd for $C_{19}H_{20}N_2O_2S$+H: 341.1324, found: 341.1335; Anal. Calcd for $C_{19}H_{20}N_2O_2S·2H_2O$: C, 60.62; H, 6.43; N, 7.44. Found: C, 60.06; H, 5.94; N, 7.51.

The identification of Example 3(b) was based on the x-ray crystallography of its (S)-mandelic acid derivative:

(2'S)-2'-hydroxy-N-[(3S)-9-methyl-6-(phenylsulfonyl)-2,3,4,9-tetrahydro-1H-carbazol-3-yl]-2-phenylethanamide:

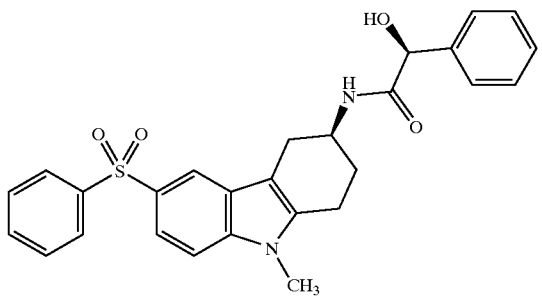

To a solution of (3S)-9-methyl-6-(phenylsulfonyl)-2,3,4,9-tetrahydro-1H-carbazol-3-amine (0.500 g, 1.47 mmol), (S)-Mandelic acid (0.224 g, 1.47 mmol), 1-hydorxytriazole (0.199 g, 1.47 mmol) and triethylamine (0.21 mL, 0.147 mmol) in dichloromethane (15.0 mL) was added 1-(3-dimethylaminopropyl)-3-ethylcarbodiimide hydrochloride (0.282 g, 1.47 mmol) at 0° C. The resulted mixture was stirred at room temperature for over night. Water (20.0 mL) and dichloromethane (15.0 mL) were added and separated. The aqueous layer was extracted with dichloromethane (2×20.0 mL). The combined organic solutions was dried ($MgSO_4$) and filtered. The filtrated was concentrated in vacuo to dryness and the residue was subjected to column chromatography (EtOAc) to give 0.544 g (78%) of colorless solid as the title compound: mp 138–140° C. (EtOAc/hex); $[α]_D$=+78° (c 0.78, CHCl$_3$); $^1$H NMR (400 MHz, CDCl$_3$) δ 8.02 (d, J=1.7 Hz, 1 H), 7.93–7.90 (m, 2 H), 7.68–7.66 (dd, J=8.6, 1.7 Hz, 1 H), 7.48–7.31 (m, 10 H), 7.25 (d, J=8.6 Hz, 1 H), 6.49 (d, J=8.0 Hz, 1 H), 5.05 (s, 1 H), 4.28 (br, 1 H), 3.57 (s, 3 H), 3.02 (dd, J=15.3, 5.1 Hz, 1 H), 2.72 (t, J=6.1 Hz, 2 H), 2.52 (dd, J=15.3, 7.6 Hz, 1 H), 2.08 (m, 1 H), 1.94 (m, 1 H); $^{13}$C NMR (100 MHz, CDCl$_3$) δ 171.9, 143.1, 139.5, 139.2, 137.2, 132.5, 131.2, 129.1, 128.8, 128.6, 127.2, 126.7, 126.6, 120.1, 118.8, 109.2, 108.2, 74.2, 45.2, 29.5, 28.0, 27.4, 19.9; IR (diffuse reflectance) 3406, 3396, 3268, 1663, 1644, 1638, 1619, 1525, 1522, 1449, 1304, 1288, 1151, 1088, 1061 cm$^{-1}$; HRMS (FAB) calcd for $C_{27}H_{26}N_2O_4S$+H 475.1691, found 475.1703; Anal. Calcd for $C_{27}H_{26}N_2O_4S·0.25H_2O$: C, 67.69; H, 5.57; N, 5.85. Found: C, 67.70; H, 5.64; N, 5.82.

Example 4
(3R)-N,9-Dimethyl-6-(phenylsulfonyl)-2,3,4,9-tetrahydro-1H-carbazol-3-amine hydrochloride:

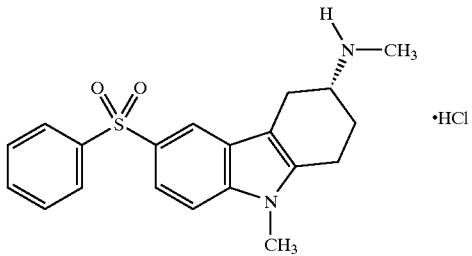

Step 1:
Following the general procedure of EXAMPLE 2(a) (step 1) and making non-critical variations, tert-butyl (3R)-9-methyl-6-(phenylsulfonyl)-2,3,4,9-tetrahydro-1H-carbazol-3-ylcarbamate was prepared as a brown solid (74%): mp 155–160° C.; $[\alpha]_D=-34°$ (c 1.01, chloroform); $^1$H NMR (400 MHz, CDCl$_3$) δ 8.11, 7.95–7.92, 7.68, 7.50–7.42, 7.30, 4.65, 4.08, 3.63, 3.09, 2.82–2.79, 2.64, 2.13, 2.02–1.96, 1.46; $^{13}$C NMR (100 MHz, CDCl$_3$) δ 155.4, 143.2, 139.2, 137.3, 132.4, 131.3, 129.0, 127.2, 126.8, 120.2, 118.9, 109.2, 108.5, 79.5, 46.0, 29.5, 28.5, 28.4, 28.0, 19.8; IR (diffuse reflectance) 1701, 1519, 1482, 1367, 1300, 1289, 1181, 1173, 1163, 1151, 731, 687, 626, 613, 607 cm$^{-1}$; HRMS (FAB) calcd for C$_{24}$H$_{28}$N$_2$O$_4$S+H 441.1848, found 441.1873; Anal. Calcd for C$_{24}$H$_{28}$N$_2$O$_4$S: C, 65.43; H, 6.41; N, 6.36. Found: C, 65.35; H, 6.38; N, 6.38.

Step 2:
A solution of tert-butyl (3R)-9-methyl-6-(phenylsulfonyl)-2,3,4,9-tetrahydro-1H-carbazol-3-ylcarbamate (1.74 g, 3.95 mmol) in DMF (13.0 mL) was added to a 0° C. suspension of 60% sodium hydride (0.38 g, 9.62 mmol) in DMF (3.0 mL) and stirred at room temperature for 1.1 hours. Methyl iodide (0.30 mL, 4.81 mmol) was added, and the reaction was stirred at room temperature for 2.0 hours. The reaction was cooled to 0° C., quenched with water and filtered. The filtrate was concentrated in vacuo, combined with the previously filtered solid and partitioned between ethyl acetate and water. The organic layer was washed with brine, dried over MgSO$_4$ and concentrated in vacuo to dryness, the residue was recrystallized from EtOAc/hexane to give 1.36 g (76%) of tert-butyl methyl [(3R)-9-methyl-6-(phenylsulfonyl)-2,3,4,9-tetrahydro-1H-carbazol-3-yl]carbamate as a colorless solid: mp 181.4–183.2° C.; $[\alpha]_D=+103°$ (c 1.02, DMSO); $^1$H NMR (400 MHz, DMSO-d$_6$) δ 8.06, 7.93–7.91, 7.62–7.53, 4.22, 3.64, 2.96–2.92, 2.84–2.79, 1.99–1.94, 1.42; $^{13}$C NMR (100 MHz, DMSO-d$_6$) δ 155.6, 142.8, 138.7, 138.0, 132.7, 130.5, 129.3, 126.7, 125.9, 119.1, 118.0, 110.0, 108.6, 78.5, 29.3, 28.5, 28.0, 26.4, 23.5, 21.2; IR (diffuse reflectance) 1684, 1481, 1448, 1398, 1378, 1364, 1357, 1304, 1184, 1149 (s), 1103, 732, 690, 622, 612 cm$^{-1}$; HRMS (FAB) calcd for C$_{25}$H$_{30}$N$_2$O$_4$S+H 455.2004, found 455.2027; Anal. Calcd for C$_{25}$H$_{30}$N$_2$O$_4$S: C, 66.05; H, 6.65; N, 6.16. Found: C, 65.99; H, 6.66; N, 6.19.

Step 3:
Following the general procedure of EXAMPLE 2 (step 2) and making non-critical variations, (3R)-N,9-dimethyl-6-(phenylsulfonyl)-2,3,4,9-tetrahydro-1H-carbazol-3-amine hydrochloride was prepared as a colorless solid (47%): mp>275° C.; $^1$H NMR (400 MHz, DMSO-d$_6$) δ 9.25, 8.11, 7.91, 7.62–7.57, 3.65, 3.42, 3.28, 2.93, 2.81, 2.66, 2.35, 1.99; $^{13}$C NMR (100 MHz, DMSO-d$_6$) δ 142.7, 138.7, 138.0, 132.8, 130.6, 129.4, 126.7, 125.6, 119.4, 117.9, 110.2, 106.2, 54.0, 29.8, 29.4, 24.8, 23.1, 19.4; IR (diffuse reflectance) 2959, 2938, 2931, 2792, 2768, 2748, 2708, 2459, 1478, 1306, 1300, 1151, 1099, 732, 624 cm$^{-1}$; HRMS (FAB) calcd for C$_{20}$H$_{22}$N$_2$O$_2$S+H 355.1480, found 355.1485; Anal. Calcd for C$_{20}$H$_{22}$N$_2$O$_2$S: C, 61.45; H, 5.93; N, 7.17. Found: C, 61.16; H, 5.93; N, 7.12.

Example 5
(3R)-9-Methyl-6-(phenylsulfonyl)-2,3,4,4a,9,9a-hexahydro-1H-carbazol-3-amine:

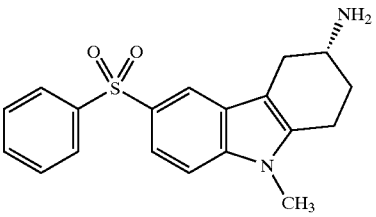

Step 1:
A freshly prepared solution of sodium cyanoborohydride (0.91 g, 14.48 mmol) in CH$_3$OH (3.0 mL) was added dropwise to a 0° C. solution of (3R)-9-methyl-6-(phenylsulfonyl)-2,3,4,9-tetrahydro-1H-carbazol-3-amine (1.02 g, 2.99 mmol) in TFA (7.5 mL), then stirred at room temperature for 3 hours. The reaction was diluted with H$_2$O (40 mL) cooled to 0° C. and made basic by the addition of 50% NaOH. The reaction mixture was extracted with EtOAc, washed with brine, dried over MgSO$_4$ and concentrated in vacuo to give a colorless foam which was recrystallized from CH$_3$OH/EtOAc to give 0.19 g (19%) of (3R)-9-methyl-6-(phenylsulfonyl)-2,3,4,4a,9,9a-hexahydro-1H-carbazol-3-amine as a colorless as a mixture of cis and trans isomers: mp 217.0–219.3° C.; MS m/z 343.2 (M$^+$+H).

5-HT$_6$ Receport Binding Assay

Growth of Cells and Membrane Preparation

Hela cells containing the cloned human 5-HT$_6$ receptor were acquired from Dr. David R. Sibley's laboratory in National Institute of Health (see Sibley, D. R., *J. Neurochemistry*, 66, 47–56, 1996). Cells were grown in high glucose Dulbecco's modified Eagle's medium, supplemented with L-glutamine, 0.5% sodium pyruvate, 0.3% penicillin-streptomycin, 0.025% G-418 and 5% Gibco fetal bovine serum and then were harvested, when confluent, in cold phosphate buffered saline.

Harvested intact cells were washed once in cold phosphate-buffered saline. The cells were pelleted and resuspended in 100 ml of cold 50 mM Tris, 5 mM EDTA and 5 mM EGTA, pH 7.4. Homogenization was with a Vir Tishear generator, 4 cycles for 30 seconds each at setting 50. The homogenized cells were centrifuged at 700 RPM (1000×g) for 10 minutes and the supernatant was removed. The pellet was resuspended in 100 ml of the above buffer and rehomogenized for 2 cycles. The rehomogenized cells were then centrifuged at 700 RPM (1000×g) for 10 minutes and the supernatant was removed. The combined supernatant (200 ml) was centrifuged at 23,000 RPM (80,000×g) for 1 hour in a Beckman Rotor (42.1 Ti). The membrane pellet was resuspended in 50–8-ml of assay buffer containing HEPES 20 mM, MgC12 10 mM, NaCl 150 mM, EDTA 1 mM, pH 7.4 and stored frozen in aliqouts at −70° C.

5-HT$_6$ Receptor Binding Assay

The radioligand binding assay used [$^3$H]-lysergic acid diethylamide (LSD). The assay was carried out in Wallac 96-well sample plates by the addition of 11 µl of the test sample at the appropriate dilution (the assay employed 11 serial concentrations of samples run in duplicate), 11 µl of radioligand, and 178 µl of a washed mixture of WGA-coated SPA beads and membranes in binding buffer. The plates were shaken for about 5 minutes and then incubated at room temperature for 1 hour. The plates were then loaded into counting cassettes and counted in a Wallac MicroBeta Trilux scintillation counter.

Binding Constant (Ki) Determination

Eleven serial dilutions of test compounds were distributed to assay plates using the PE/Cetus Pro/Pette pipetter. These dilutions were, followed by radioligand and the bead-membrane mixture prepared as described above. The specifically bound cpm obtained were fit to a one-site binding model using GraphPad Prism ver. 3.0. Estimated $IC_{50}$ values were converted to Ki values using the Cheng-Prusoff equation (Cheng, Y. C. et al., *Biochem. Pharmacol.*, 22, 3099–108, 1973). The Examples have Ki values from about 2.9 nM to about 58 nM.

What is claimed:

1. A compound of formula I

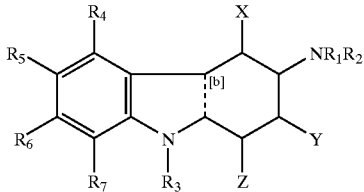

Formula I wherein

- - - [b] is a single or double bond;

Each X, Y, and Z is independently selected from H, —OH, —O-alkyl, and —O-substituted alkyl;

$R_1$ is selected from H, alkyl, substituted alkyl, cycloalkyl, substituted cycloalkyl, and aryl;

$R_2$ is selected from H, alkyl, substituted alkyl, cycloalkyl, substituted cycloalkyl, and aryl;

$R_3$ is selected from H, alkyl, substituted alkyl, cycloalkyl, substituted cycloalkyl;

Each $R_4$, $R_5$, $R_6$, and $R_7$ is independently selected from H, halogen, aryl, —CN, —NO$_2$, alkyl, substituted alkyl, cycloalkyl, substituted cycloalkyl, and —S(O)$_n$aryl, provided that one of $R_4$, $R_5$, $R_6$, and $R_7$ is —S(O)$_n$aryl, and that at least one of $R_4$, $R_5$, $R_6$, and $R_7$ is H;

n is 0, 1, or 2; and pharmaceutically acceptable salts thereof.

2. A compound of claim 1 having the Formula Ib

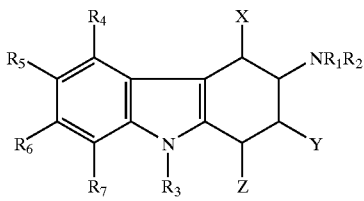

Formula Ib wherein

Each X, Y, and Z is independently selected from H, —OH, —O-alkyl, and —O-substituted alkyl;

$R_1$ is selected from H, alkyl, substituted alkyl, cycloalkyl, substituted cycloalkyl, and aryl;

$R_2$ is selected from H, alkyl, substituted alkyl, cycloalkyl, substituted cycloalkyl, and aryl;

$R_3$ is selected from H, alkyl, substituted alkyl, cycloalkyl, substituted cycloalkyl;

Each $R_4$, $R_5$, $R_6$, and $R_7$ is independently selected from H, halogen, aryl, —CN, —NO$_2$, alkyl, substituted alkyl, cycloalkyl, substituted cycloalkyl, and —S(O)$_n$aryl, provided that one of $R_4$, $R_5$, $R_6$, and $R_7$ is —S(O)$_n$aryl, and that at least one of $R_4$, $R_5$, $R_6$, and $R_7$ is H;

n is 0, 1, or 2; and pharmaceutically acceptable salts thereof.

3. The compound of claim 2, wherein one of $R_1$ and $R_2$ is H, and the other is H, alkyl, or substituted alkyl.

4. The compound of claim 3, wherein $R_5$ is aryl S(O)$_n$—, and wherein $R_4$, $R_6$, and $R_7$ are H.

5. The compound of claim 4, wherein n is 2.

6. The compound of claim 5, wherein $R_3$ is H or alkyl.

7. The compound of claim 6, wherein the compound is (rac)-6-(phenylsulfonyl)-2,3,4,9-tertrahydro-1H-carbazol-3-amine;

(3S)-6-(phenylsulfonyl)-2,3,4,9-tertrahydro-1H-carbazol-3-amine;

(3R)-6-(phenylsulfonyl)-2,3,4,9-tertrahydro-1H-carbazol-3-amine;

(3S)-9-methyl-6-(phenylsulfonyl)-2,3,4,9-tertrahydro-1H-carbazol-3-amine;

(3R)-9-methyl-6-(phenylsulfonyl)-2,3,4,9-tertrahydro-1H-carbazol-3-amine;

(3R)-N,9-dimethyl-6-(phenylsulfonyl)-2,3,4,9-tetrahydro-1H-carbazol-3-amine;

or a pharmaceutically acceptable salt thereof.

8. The compound of claim 7, wherein the stereochemistry at the C-3 position is R.

9. The compound of claim 8, wherein the compound is (3R)-6-(phenylsulfonyl)-2,3,4,9-tertrahydro-1H-carbazol-3-amine;

(3R)-9-methyl-6-(phenylsulfonyl)-2,3,4,9-tertrahydro-1H-carbazol-3-amine;

(3R)-N,9-dimethyl-6-(phenylsulfonyl)-2,3,4,9-tetrahydro-1H-carbazol-3-amine;

or a pharmaceutically acceptable salt thereof.

10. A pharmaceutical composition comprising a compound according to claim 2.

11. A method for treating a disease or condition, in a mammal in need thereof, selected from the group consisting of anxiety, depression, schizophrenia, Alzheimer's disease, stress-related disease, panic, a phobia, obsessive compulsive disorder, obesity, post-traumatic stress syndrome, or epilepsy comprising administering to the mammal a therapeutically effective amount of compound according to claim 2.

12. The method according to claim 11, wherein said compound is administered rectally, topically, orally, sublingually, or parenterally.

13. The method according to claim 11, wherein said compound is administered from about 0.001 to about 100 mg/kg of body weight of said mammal per day.

14. The method according to claim 11, wherein said compound is administered from about 0.1 to about 50 mg/kg of body weight of said mammal per day.

15. The compound of claim 2, wherein the compound includes at least one atom selected from Carbon-11, Nitrogen-13, Oxygen-15, and Fluorine-18.

16. A compound of claim 1 having the Formula Ia

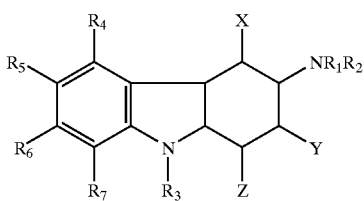

Formula Ia wherein
- Each X, Y, and Z is independently selected from H, —OH, —O-alkyl, and —O-substituted alkyl;
- $R_1$ is selected from H, alkyl, substituted alkyl, cycloalkyl, substituted cycloalkyl, and aryl;
- $R_2$ is selected from H, alkyl, substituted alkyl, cycloalkyl, substituted cycloalkyl, and aryl;
- $R_3$ is selected from H, alkyl, substituted alkyl, cycloalkyl, substituted cycloalkyl;
- Each $R_4$, $R_5$, $R_6$, and $R_7$ is independently selected from H, halogen, aryl, —CN, —NO$_2$, alkyl, substituted alkyl, cycloalkyl, substituted cycloalkyl, and —S(O)$_n$aryl, provided that one of $R_4$, $R_5$, $R_6$, and $R_7$ is —S(O)$_n$aryl, and that at least one of $R_4$, $R_5$, $R_6$, and $R_7$ is H;
- n is 0, 1, or 2; and pharmaceutically acceptable salts thereof.

17. The compound of claim 16, wherein one of $R_1$ and $R_2$ is H, and the other is H, alkyl, or substituted alkyl.

18. The compound of claim 17, wherein $R_5$ is arylS(O)$_n$—, and wherein $R_4$, $R_6$, and $R_7$ are H.

19. The compound of claim 18, wherein n is 2.

20. The compound of claim 19, wherein $R_3$ is H or alkyl.

21. The compound of claim 20, wherein the compound is selected from
- (3R)-9-methyl-6-(phenylsulfonyl)-2,3,4,4a,9,9a-hexahydro-1H-carbazol-3-amine;
- (3S)-9-methyl-6-(phenylsulfonyl)-2,3,4,4a,9,9a-hexahydro-1H-carbazol-3-amine;
- (3R)-6-(phenylsulfonyl)-2,3,4,4a,9,9a-hexahydro-1H-carbazol-3-amine;
- (3S)-6-(phenylsulfonyl)-2,3,4,4a,9,9a-hexahydro-1H-carbazol-3-amine;
- (rac)-6-(phenylsulfonyl)-2,3,4,4a,9,9a-hexahydro-1H-carbazol;
- (3S)-N,9-dimethyl-6-(phenylsulfonyl)-2,3,4,4a,9,9a-hexahydro-1H-carbazol-3-amine;
- (3R)-N,9-dimethyl-6-(phenylsulfonyl)-2,3,4,4a,9,9a-hexahydro-1H-carbazol-3-amine;

and pharmaceutically acceptable salts thereof.

22. The compound of claim 20, wherein the stereochemistry at the C-3 position is R.

23. The compound of claim 22, wherein the compound is
- (3R)-9-methyl-6-(phenylsulfonyl)-2,3,4,4a,9,9a-hexahydro-1H-carbazol-3-amine;

or a pharmaceutically acceptable salt thereof.

24. A pharmaceutical composition comprising a compound according to claim 16.

25. A method for treating a disease or condition, in a mammal in need thereof, selected from the group consisting of anxiety, depression, schizophrenia, Alzheimer's disease, stress-related disease, panic, a phobia, obsessive compulsive disorder, obesity, post-traumatic stress syndrome, or epilepsy comprising administering to the mammal a therapeutically effective amount of compound according to claim 16.

26. The method according to claim 25, wherein said compound is administered rectally, topically, orally, sublingually, or parenterally.

27. The method according to claim 25, wherein said compound is administered from about 0.001 to about 100 mg/kg of body weight of said mammal per day.

28. The method according to claim 25, wherein said compound is administered from about 0.1 to about 50 mg/kg of body weight of said mammal per day.

29. The compound of claim 16, wherein the compound includes at least one atom selected from Carbon-11, Nitrogen-13, Oxygen-15, and Fluorine-18.

* * * * *